(12) United States Patent
Hou et al.

(10) Patent No.: US 11,264,121 B2
(45) Date of Patent: Mar. 1, 2022

(54) REAL-TIME INDUSTRIAL PLANT PRODUCTION PREDICTION AND OPERATION OPTIMIZATION

(71) Applicant: Accenture Global Solutions Limited, Dublin (IE)

(72) Inventors: Fang Hou, Beijing (CN); Yikai Wu, Beijing (CN); Kexin Ren, Beijing (CN); Hui Shen, Beijing (CN); Xinyong Min, Beijing (CN); Xiaopei Cheng, Beijing (CN)

(73) Assignee: Accenture Global Solutions Limited, Dublin (IE)

( * ) Notice: Subject to any disclaimer, the term of this patent is extended or adjusted under 35 U.S.C. 154(b) by 492 days.

(21) Appl. No.: 16/326,859

(22) PCT Filed: Aug. 23, 2016

(86) PCT No.: PCT/CN2016/096386
§ 371 (c)(1),
(2) Date: Feb. 20, 2019

(87) PCT Pub. No.: WO2018/035718
PCT Pub. Date: Mar. 1, 2018

(65) Prior Publication Data
US 2019/0198136 A1  Jun. 27, 2019

(51) Int. Cl.
*G05B 13/02* (2006.01)
*G05B 13/04* (2006.01)
(Continued)

(52) U.S. Cl.
CPC ......... *G16C 20/70* (2019.02); *G05B 13/0265* (2013.01); *G05B 13/048* (2013.01);
(Continued)

(58) Field of Classification Search
CPC .... G16C 20/70; G16C 20/90; G05B 13/0265; G05B 13/048; G06F 17/18; G06N 7/005
See application file for complete search history.

(56) References Cited

U.S. PATENT DOCUMENTS 7,085,615 B2 *  8/2006  Persson ............... G05B 13/048
                                                    700/108
8,341,106 B1 * 12/2012  Scolnicov .............. G01F 1/50
                                                    706/47
(Continued)

FOREIGN PATENT DOCUMENTS

CA   2035672 A1 *  9/1991  ............. G06Q 10/06
CN   1942878 A       4/2007
(Continued)

OTHER PUBLICATIONS

Raul Rojas, The Kalman Filter, Published 2002. Semantic Scholar (Year: 2002).*

(Continued)

*Primary Examiner* — Natalie Huls
(74) *Attorney, Agent, or Firm* — Crowell & Moring LLP

(57) ABSTRACT

Direct measurement and simulation of real-time production rates of chemical products in complex chemical plants is complex. A predictive model developed based on machine learning algorithms using historical sensor data and production data provides accurate real-time prediction of production rates of chemical products in chemical plants. An optimization model based on machine learning algorithms using clustered historical sensor data and production data provides optimal values for controllable parameters for production maximization.

18 Claims, 17 Drawing Sheets

(51) Int. Cl.
  *G06F 17/18* (2006.01)
  *G06N 7/00* (2006.01)
  *G16C 20/70* (2019.01)
  *G16C 20/90* (2019.01)

(52) U.S. Cl.
  CPC ............ *G06F 17/18* (2013.01); *G06N 7/005* (2013.01); *G16C 20/90* (2019.02)

(56) References Cited

U.S. PATENT DOCUMENTS

| | | | |
|---|---|---|---|
| 11,080,613 B1* | 8/2021 | Camara | G06N 20/00 |
| 2003/0139828 A1 | 7/2003 | Ferguson et al. | |
| 2004/0147817 A1 | 7/2004 | Dewing et al. | |
| 2005/0187745 A1 | 8/2005 | Lurie et al. | |
| 2006/0058898 A1 | 3/2006 | Emigholz et al. | |
| 2006/0218107 A1* | 9/2006 | Young | G05B 13/027 706/13 |
| 2010/0145891 A1 | 6/2010 | Dhanekula et al. | |
| 2010/0161810 A1 | 6/2010 | Vaidyanathan et al. | |
| 2011/0166684 A1 | 7/2011 | Moyne et al. | |
| 2012/0143800 A1 | 6/2012 | Zhou et al. | |
| 2013/0066471 A1* | 3/2013 | Wang | G05B 13/024 700/275 |
| 2013/0069792 A1 | 3/2013 | Blevins et al. | |
| 2014/0143188 A1 | 5/2014 | Mackey et al. | |
| 2016/0165472 A1* | 6/2016 | Gopalakrishnan | H04W 16/28 455/67.11 |
| 2016/0328654 A1* | 11/2016 | Bauer | G06K 9/6267 |
| 2017/0249559 A1* | 8/2017 | Herzog | G06N 7/005 |
| 2017/0372222 A1* | 12/2017 | Kollia | G06N 20/00 |
| 2018/0357261 A1* | 12/2018 | Danichev | G06F 16/215 |

FOREIGN PATENT DOCUMENTS

| | | |
|---|---|---|
| CN | 101187803 A | 5/2008 |
| CN | 101777147 A | 7/2010 |
| CN | 101842756 A | 9/2010 |
| CN | 101965569 A | 2/2011 |
| CN | 102110187 A | 6/2011 |
| CN | 102750454 A | 10/2012 |
| CN | 103198178 A | 7/2013 |
| CN | 103443296 A | 12/2013 |
| CN | 104062904 A | 9/2014 |
| CN | 104778298 A | 7/2015 |
| CN | 105122153 A | 12/2015 |
| CN | 105807741 A | 7/2016 |
| EP | 0 906 593 | 4/1999 |
| WO | WO 97/49011 | 12/1997 |

OTHER PUBLICATIONS

Office Action, and Search Report, in China Application No. 201680088673.4, including summarized English translation, dated Aug. 6, 2021, 8 pages.

Author: Wang Yunbo, Advisor: Wang Zibin, "Calderon Technique Based Integral Equation Methods in Computational Electromagnetics", Master Thesis for Professional Degree, University of Electronic Science and Technology of China, dated May 15, 2014, 66 pages.

Warne et al., "Development of a hybrid PCA-ANFIS measurement system for monitoring product quality in the coating industry", 2004 IEEE International Conference on Systems, Man and Cybernetica, 6 pages, dated Dec. 31, 2004.

International Search Report and Written Opinion of the International Search Authority dated May 25, 2017 in International Application No. PCT/CN2016/096386 (English language) (9 pp.).

Notification of International Preliminary Report on Patentability issued in corresponding PCT application No. PCT/CN2016/096386 dated Feb. 26, 2019, 6 pages.

* cited by examiner

REAL-TIME INDUSTRIAL PLANT PRODUCTION PREDICTION AND OPERATION OPTIMIZATION

CROSS-REFERENCE TO RELATED APPLICATION

This application is the U.S. National Stage of International Application No. PCT/CN2016/096386, filed on Aug. 23, 2016.

TECHNICAL FIELD

This disclosure is related to production control of chemical products in chemical plants based on machine learning algorithms.

BACKGROUND

Industrial plants such as chemical plants are complex systems with hundreds and thousands of distributed sensors for monitoring the operational status of the plants. Operators of a chemical plant often desire to gain knowledge of production rates of chemical products of the plant in real-time. In many cases, however, direct and accurate measurement of production data in real-time may be difficult or impossible even when the sensor parameters may be measured and recorded in real-time. Accurate data is important for optimal predictive control of the chemical plants. Due to the complexity and chaotic nature of a chemical plant, prediction of the production data using measured sensor parameters and based on simulative techniques may not be accurate or even practical.

DETAILED DESCRIPTION

Chemical plants are complex systems with dynamics that are difficult to control in an accurate manner. Operators of a chemical plant may only be capable of exerting a limited control over the chemical processes within the plant via a number of control devices such as flow valves and heaters. Due to the chaotic nature of chemical reaction processes, production rates of chemical products may be predicted using controllable parameters associated with these control devices based on traditional domain model but with low accuracy. Even though a typical chemical plant is further installed with a large number of sensors to monitor the operation of the plant, it is still difficult to deterministically establish a simulative model for the complex chemical processes in large reactors based on these real-time sensor data. Production rates of chemicals may be more accurately predicted based on models established through machine learning algorithms using historical production data and corresponding historical sensor data, as will be described in detail below. While the embodiments below use production of styrene in a styrene plant as an example, the underlying principles are not so limited and are intended to be applicable to other chemical plants and other complex industrial processes.

Figure 1A:
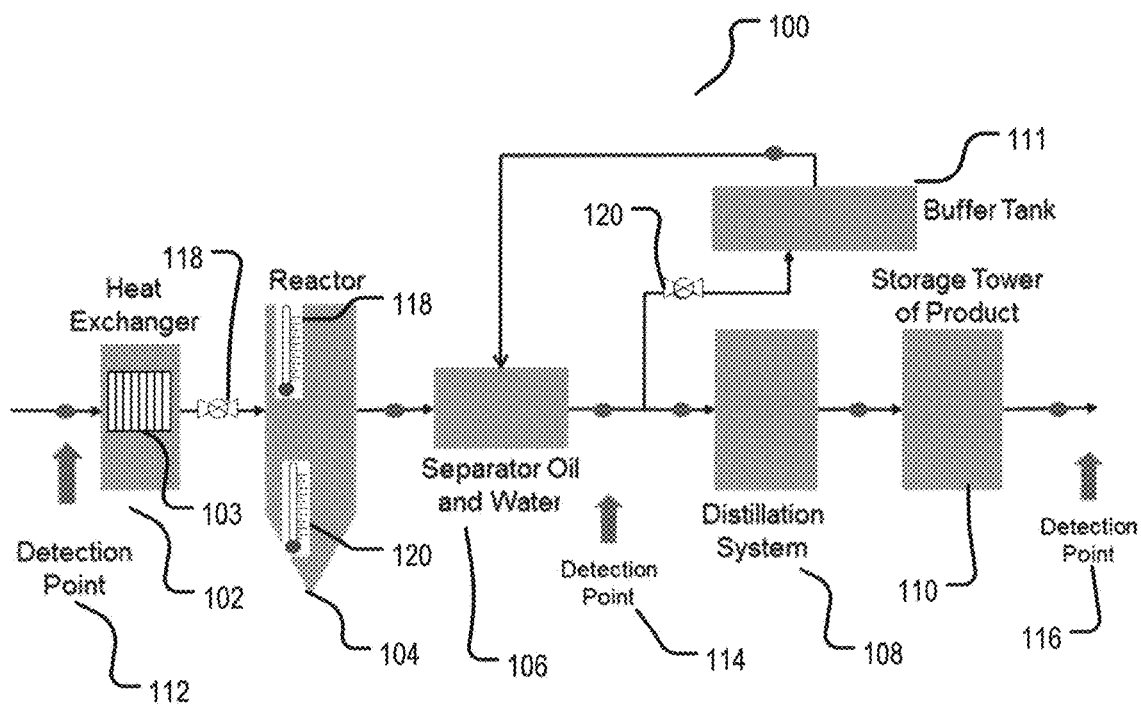
FIG. 1A shows a schematic diagram for a chemical plant.

FIG. 1A shows a simplified schematic of an exemplary chemical plant 100 for styrene production containing a heat exchanger 102, a reactor 104, a water/oil separator 106, a distillation system 108, a storage tower 110, and a buffer tank 111. Ethylene, Benzene, or other hydrocarbon feed stock may be pumped into the heat exchanger 102, which may include heating element 103 for heating the hydrocarbon mixture. The heating element may be, for example, in the form of serpentine lines or pipes of steam through a heat-exchanging chamber confining the hydrocarbon mixture. The reactor 104 includes a reaction chamber for producing styrene from the hydrocarbon mixture or hydrocarbon feed stock. Other material, such as various catalysts, may be added into the reactor to speed up and maximize chemical conversion from hydrocarbon mixture to styrene. The reaction product mixture containing styrene and other byproducts may be guided through the water/oil separator 106, in which water is removed from the rest of the reaction product mixture. Water/oil separation may be done in a loop in which the oil composition containing styrene is collected into the buffer tank 111. The oil composition with water separated from it may then be distilled in the distillation system 108. Various components in the oil composition may be further separated and stored in the storage tower 110. In particular, styrene may be one of the distilled products and be stored in one of the storage tanks in the storage tower 110.

Figure 1B:
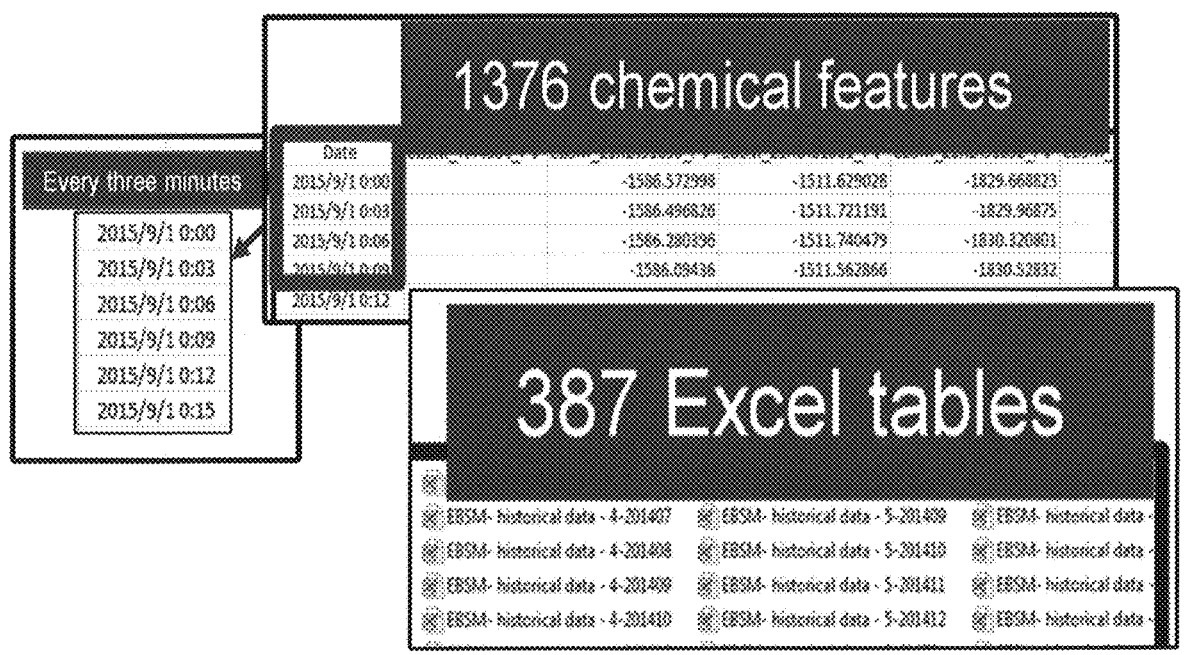
FIG. 1B shows various sensor parameters that may be collected during the operation of the chemical plant of FIG. 1A.

A chemical plant, such as the one illustrated in 100 of FIG. 1A, is a complex system and is typically installed with hundreds, if not thousands of sensors for monitoring the operating status of various subsystems of the plant and the plant as a whole. These sensors, in a styrene plant for example, may include but are not limited to thermocouples (or other temperature sensing device), pressure sensors, and flow meters. They may be installed at various locations throughout the plant. For example, in FIG. 1A, reactor 104 may be installed with thermocouples 118 and 120 at different locations in the reactor. Flow meters may be installed throughout the plant, at positions shown, for example, as dots along the chemical flow path represented by lines with arrows. Those of ordinary skill in the art understand that the illustration of FIG. 1A is extremely simplified, and only a few of the hundreds or thousands of sensors are shown as examples. For illustrative purposes, a snapshot of a subset of recorded sensor parameters in a real styrene plant is shown in FIG. 1B. Each of these sensors measures one parameter. The measurement may be made and recorded automatically at various predetermined frequency (or time interval). Some of the parameters, however, may need to be measured manually rather than automatically. Those parameters thus may not be available in real-time.

While the sensors described above provide the plant operator a view or a snapshot into the status of various components, other devices may be installed to give control of the plant operation to the operator. For example, flow of gaseous or liquid material may be controlled by various valves installed in the system, such as 118 and 120 of FIG. 1A. Local temperature may be directly controlled by tuning the heating power of heating elements in, for example, the heat exchanger 102. Some of the sensors are installed in the proximity of the control devices and thus directly measure the impact of the control devices. The parameters measured by these sensors may be referred to as controllable parameters. For example, a thermocouple may be installed in the heat exchanger near where the heating element is located. The parameter measured by that thermocouple is thus controllable by the heating elements of the heat exchanger. For another example, a flow meter may be installed directly after a valve that adjusts the flow of certain chemical. That flow meter thus measures a controllable parameter because that parameter is directly correlated with the valve being controlled and adjusted by the operator. Other parameters measured by other sensors may be referred to as uncontrollable parameters because while they may be affected by the controllable devices but they are not in close proximity of the controllable devices and thus they are at most weakly correlated with the adjustment of the controllable devices.

Real-time production of a certain chemical is usually one of the most critical data that the plant operator desires to know. Real-time production data, such as the production rate of styrene in a styrene plant, however, may not be easily obtained in real-time from any directly measured sensor parameters. Accurate estimate of styrene production may involve labor-intensive manual measurement and laboratory analysis of product that may only be made sparsely. For example, productivity (interchangeably used with "production rate") of styrene in some plants is only estimated manually a couple of times a day during continuous operation. Further, chemical plants such as the styrene plant illustrated in FIG. 1A are complex systems involving processes that are often chaotic and not subject to deterministic mathematical description. The productivity of styrene, for example, may not even be subject to a simulative model that is comprehensive enough to capture necessary dynamics in the plant to give meaningful prediction. Thus, accurate real-time styrene productivity estimate may not rely on either direct measurement or simulation.

In the embodiments described below, accurate estimate of production of chemical product, such as styrene, as a function of sensor parameters may be based on machine learning algorithms using historical data (both historical sensor data and manually measured sparse historical production data for the chemical product) and a resulting predictive model, referred to herein as a Production Index (PI) model. Using the PI model, productivity of a chemical product may be accurately predicted in real-time based on a subset of sensor parameters. The plant operator thus may keep track of the production of chemicals, such as styrene, in real-time. As will become clear to those of ordinary skill in the art, the entire set of sensor parameters are not completely independent. Neither are they completely correlated. Some of the sensor parameters may be somewhat correlated. For example, two thermocouples 118 and 120 in different locations in the reactor 104 may not be completely independent. They may be somewhat correlated in that a raise in temperature measured by one thermocouple may mean some other amount of delayed raise in the temperature measured by the other thermocouple. As will become clearer later in this disclosure, the PI model development essentially keeps most independent and weakly correlated parameters. If one parameter is strongly correlated with another parameter, one of them may be removed from the PI model because the information provided by one of them may be largely redundant.

Further, historical data may be modeled to extract correlation between the real-time controllable sensor parameters and production of the chemical product. The correlation may vary according to some plant operation condition. The plant operation condition may be represented by combinational values of a few other critical uncontrollable sensor parameters, herein referred to as operation condition sensor parameters. Thus, historical data, including the historical sensor data and historical production data of the chemical product may be clustered based on the values of the operation condition sensor parameters. Each cluster may be modeled to provide optimal values for the controllable sensor parameters for maximizing the production of the chemical product. The control devices of the chemical plant may thus be adjusted according to the optimal values of the controllable sensor parameters for a corresponding operation condition that the plant is in.

The real-time predictive modeling and real-time production optimization based on machine learning algorithms may be further combined to provide prediction and optimization with improving accuracy as more historical sensor and production data is collected during the operation of the plant under optimal condition according the optimization model.

Figure 2:
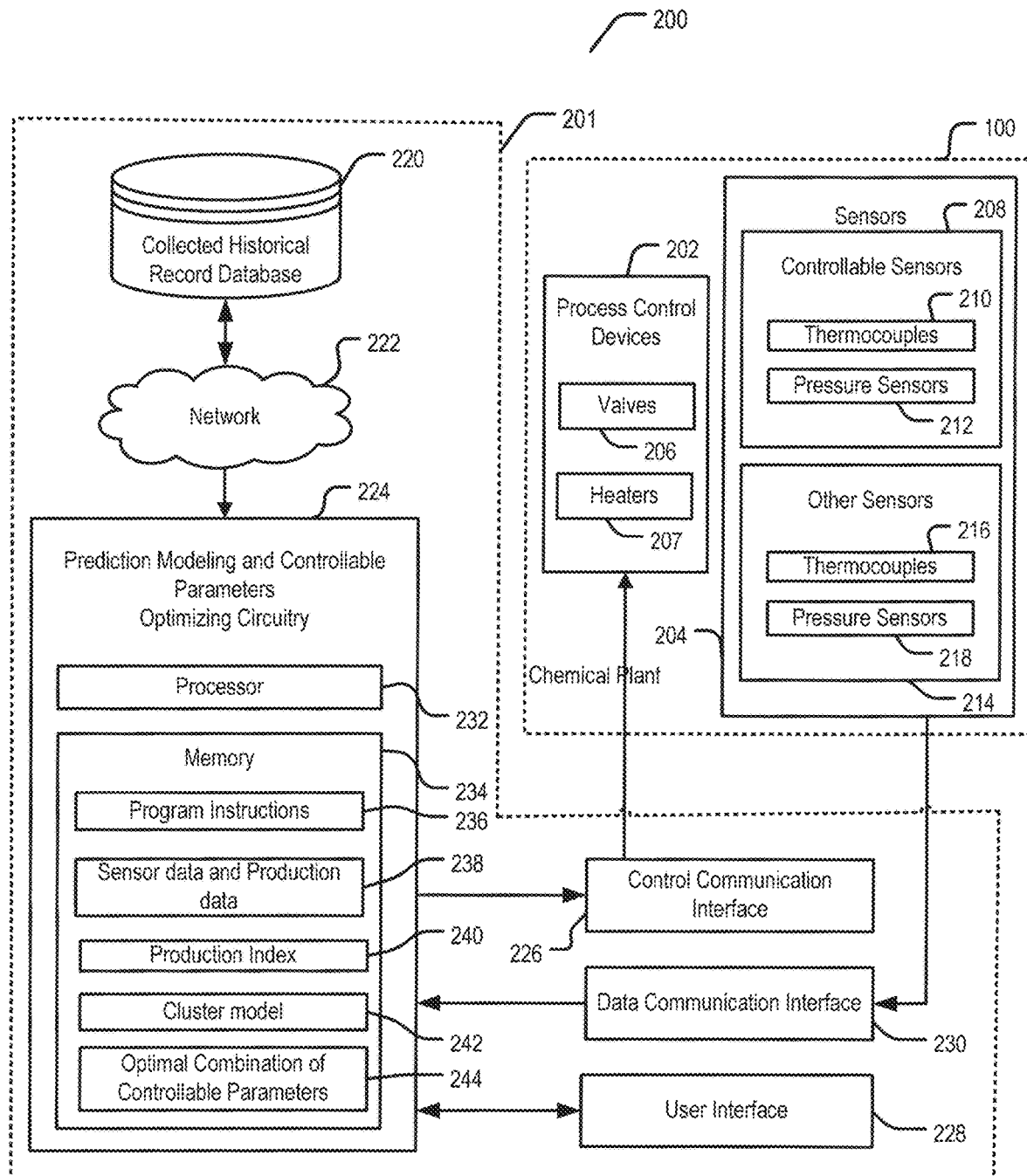
FIG. 2 shows a system for predictive production modeling and optimal control of a chemical plant.

FIG. 2 shows a system 200 for implementing the chemical production prediction and optimization. The system 200 includes a computing subsystem 201 and the chemical plant 100. The chemical plant 100 includes process control devices 202 (herein referred to interchangeably as control devices) and sensors 204. These control devices and sensors are installed throughout the chemical plant 100. The control devices 202, for example, may be adjustable valves 206 for controlling the flow of various chemicals either in gaseous or liquid forms and heaters 207 for controlling various local temperatures. The sensors 204 measure various sensor parameters and may include controllable sensors 208 such as thermocouple 210 and pressure sensor 212. These controllable sensors monitor controllable parameters that are directly controlled by the process control devices 202. The sensors 204 may further include other sensors 214 such as thermocouple 216 and pressure sensor 218 that measures parameters at locations that are not directly controlled by the control devices 202.

The computing subsystem 201 may include a database 220, a communication network 222, a circuitry 224, a control communication interface 226, a user interface 228, and a data communication interface 230. The database 220 may hold historical sensor data and historical production data and may be in communication with the circuitry 224 via the communication network 222. The computer network may be any type of wireline or wireless network known or unknown in the art. The circuitry 224 may be in communication with the control devices 202 of the chemical plant 100 via the control communication interface 226. The circuitry 224 may further be in communication with the sensors 204 of the chemical plant 100 and obtain sensor parameters measured in real-time via the data communication interface 230. The circuitry 224 may further obtain input from and display data to users via the user interface 228.

The circuitry 224 may include hardware, software, and data structure designed for developing predictive model of production of the chemical product and clustered optimization model for maximizing the production of the chemical product. The circuitry 224 may include one more processor 232 and memory 234. The memory may store program instructions 236 executable by the CPU 232, sensor data and production data for the chemical product 238 (including both historical and real-time data), the Product Index (PI) model 240 for real-time prediction of the production of the chemical product, the cluster model 242, and the optimal controllable parameter values for each cluster 244.

Figure 3:
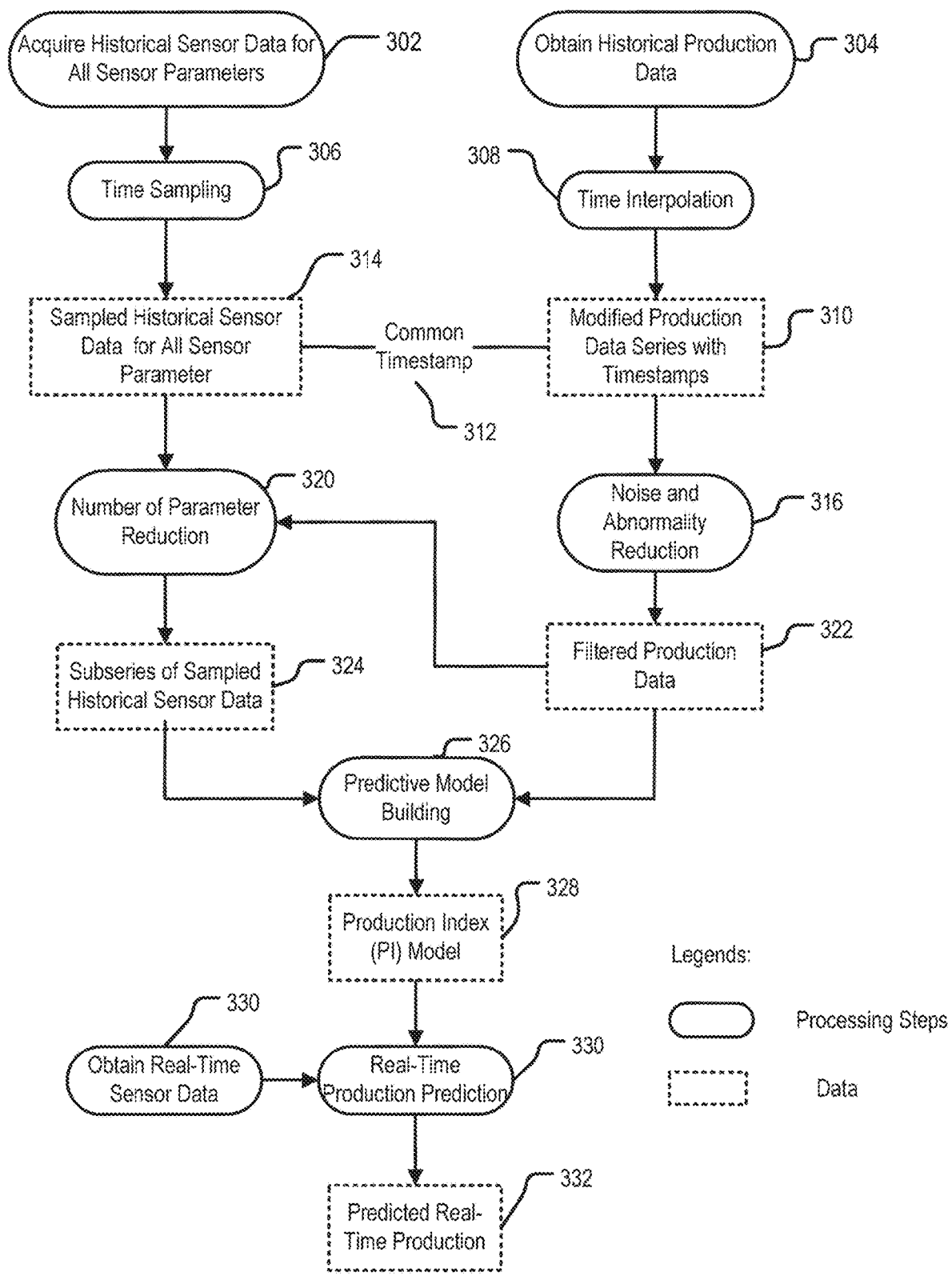
FIG. 3 is a process flow chart and data chart for an embodiment of predictive modeling of production of chemical product in a chemical plant.

FIG. 3 illustrates an exemplary implementation for developing a predictive model based on machine learning algorithms using historical sensor data and historical production data. FIG. 3 is both a flow chart of building the predictive model and a dependency chart for various data. FIG. 3 tracks separately the historical sensor data for the sensor parameters and historical production data of, e.g., styrene production. As descripted earlier, while the historical sensor data may be automatically measured and acquired from various sensors relatively frequently, the historical production data measurement may be indirect, manual, and labor intensive and thus is obtained infrequently. For example, typical historical sensor data may be recorded every second or every minute whereas the historical production data may be obtained by chemical test and analysis and recorded much less frequently, e.g., every 8 hours, during the operation of the chemical plant for producing the chemical product.

In block 302 and block 304 of FIG. 3, historical sensor data and historical production data are respectively obtained, both from the historical database of 220 in FIG. 2. For establishing an accurate predictive model for the production of the chemical product based on machine learning algorithms uing the historical data, the historical sensor data and the historical production data is preferably normalized to a same series of timestamps prior to being used for modeling. Thus, a combination of time-sampling of the historical sensor data and time-interpolation of the historical production data may be performed to provide a historical data set of normalized timestamps. For example, the normalized timestamps may correspond to historical data on a per-hour basis. Thus, in Block 306, the sampling of the historical sensor data that are measured at higher frequency may be a simple down sampling in time. In block 308, the interpolation of the sparse historical production data may be based on various interpolation algorithms such as the Local Weighted Scatterplot Smoothing (LOWESS) algorithm that will be described in more detail below. Following the processing in block 306 and 308, the sampled historical sensor data 314 for all sensor parameters and the modified production data 310 are placed on a common series of predefined timestamps 312.

In block 316, the modified production data is further processed for noise and abnormality reduction based on, e.g., a Kalman filtering algorithm, as will be described in more detail below. In particular, abnormal historical production data (due to for example, human error in manual estimation and recording of the production data) adversely affect the accuracy of the predictive model and may be effectively recognized and corrected based on algorithms such as Kalman filtering. The noise and abnormality-reduced modified production data, herein referred to as the filtered production data 322, is obtained following block 316.

In block 320, the number of parameters may be reduced using a dimensionality reduction algorithm, such as Principle Component Analysis (PCA) and Random Forest Algorithm (RFA), both to be described in more detail below. These dimensionality reduction algorithms explore the correlation and dependencies between the sensor parameters, rank and retain only the parameters that are most independent in affecting the filtered production data. As a result of the dimensionality reduction, the time-sampled historical sensor data for all sensor parameters are reduced to a subseries of sampled historical sensor data 324 under the same common timestamps but with many parameters removed.

In block, 326, predictive model or Production Index (PI) model may be built using machine learning algorithms using the subseries of sampled historical sensor data 324 and the filtered production data 322. The input to the established PI model may be the sensor parameters retained after the dimensionality reduction of 320. The predictive output of the PI model may be the predicted production for the chemical product. The building of the PI model, may be based on, for example, a Generalized Linear Regression Modeling (GLRM) technique, as will be described in more detail below.

In block 330, real-time measurement for the dimensionality reduced sensor parameters may be obtained from the chemical plant. The real-time sensor data may be input into the PI mode in block 330. The predicted real-time production 332 may thus be obtained based on the PI model.

Figure 4:
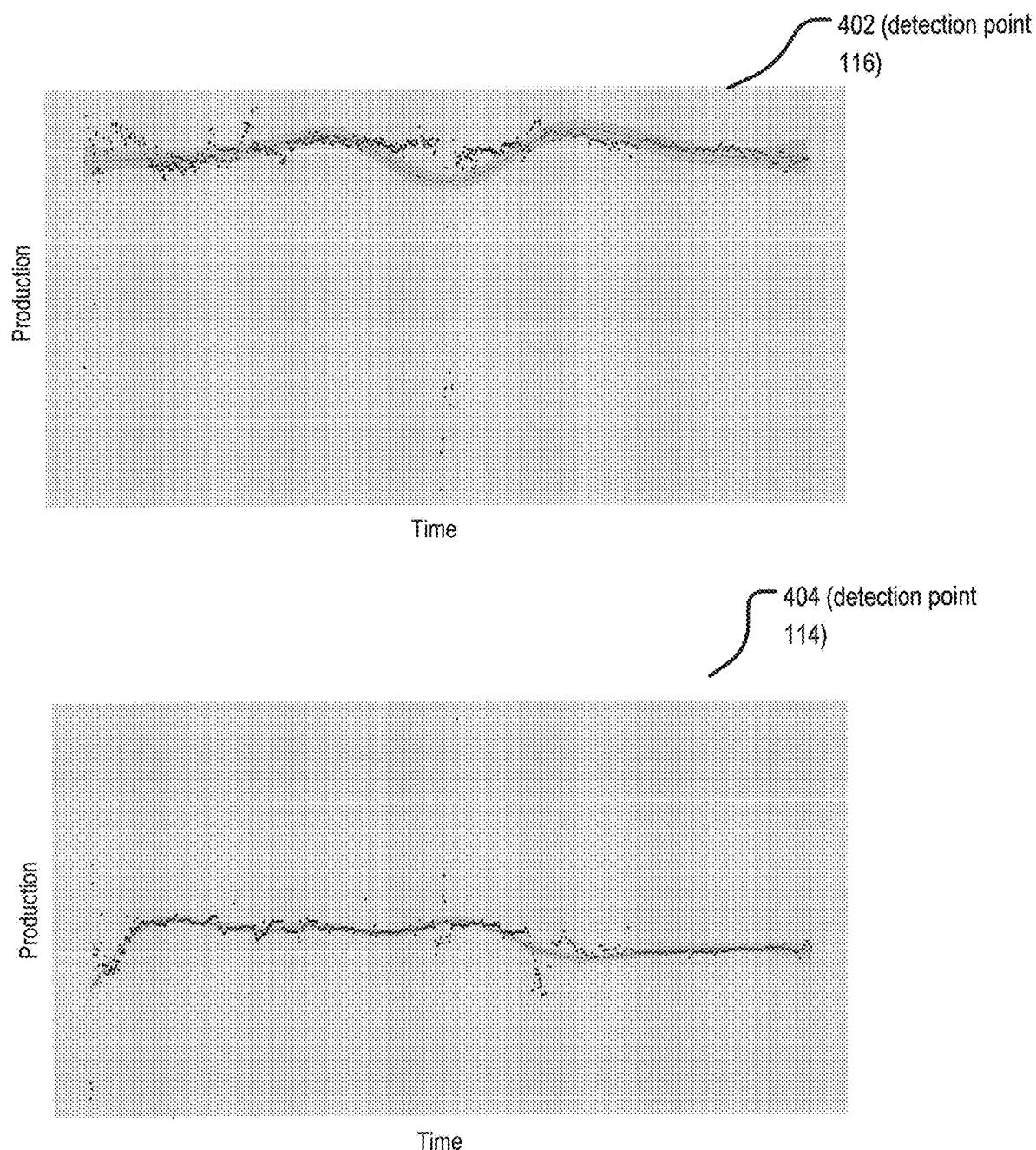
FIG. 4 shows unprocessed historical production data of a chemical plant.

FIG. 4 shows exemplary historical production data that may be used as training data in the PI model building in FIG. 3. For example, the data shown in FIG. 4 was historical data of styrene production obtained via manual analysis every 8 hours during a period of operation of a styrene plant. Data set 402 was obtained by manual analysis carried out at the detection point 116 of FIG. 1 whereas the data set 404 was obtained by manual analysis at the detection point 114 of FIG. 1.

Figure 5:
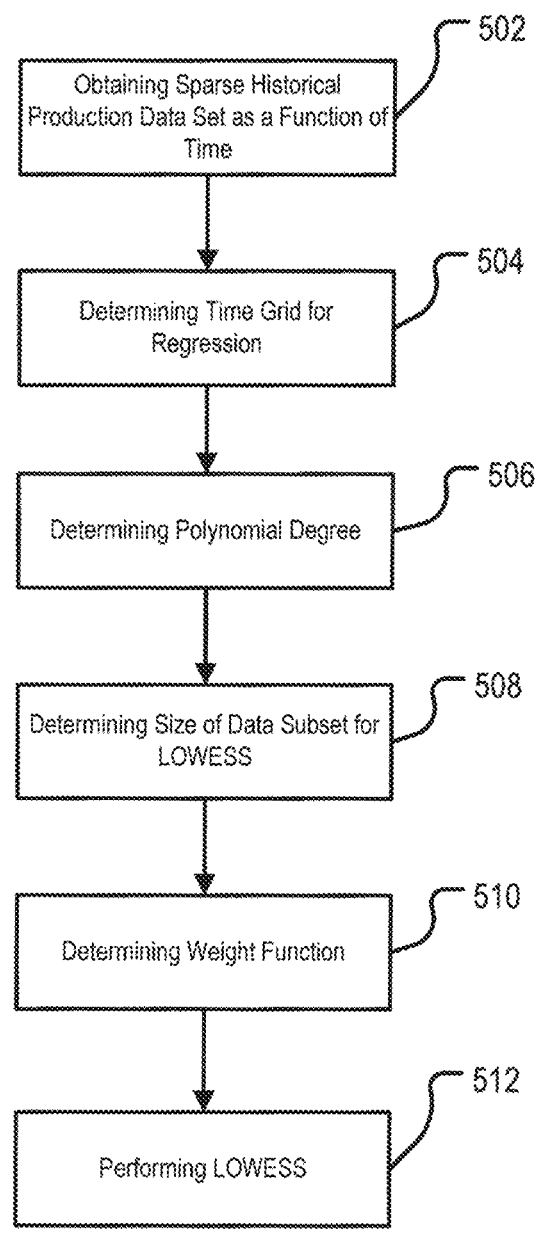
FIG. 5 is a flow chart of a method for interpolating the historical production data.

FIG. 5 shows an example implementation of the time interpolation step 308 of FIG. 3 for the historical production data such as 402 and 404 of FIG. 4. To derive an accurate predictive model, sparse historical data such as the manually obtained production data described above may be time-interpolated to replenish data in between sparse timestamps prior to model development such that these parameters appear with same timestamps as the sampled historical sensor data having a chosen sampling frequency (such as one data point per hour). The data may be interpolated using various algorithms. For example, the interpolation may be based on some local regression algorithms. In particular, the interpolation may be based on Local Weighted Scatterplot Smoothing (LOWESS), also known as locally weighted polynomial regression.

Specifically, as shown in FIG. 5 and in block 502, the sparse historical production data is obtained as input for time-interpolation. In step 504, a time grid is determined. The time grid, for example, may correspond to every hour in the period of time of operation of the plant during which the historical data were collected. For each point in the time grid, a fitting based on a low-degree polynomial with polynomial degree determined in block 506 may then be performed at block 512 with explanatory variable values (time variable in this case) near the point whose response is being interpolated. The fitting uses a local subset of data with the size of the subset (in terms of how many time grid points near the data point to be interpolated may be used) determined in block 508. The polynomial fitting may be based on weighted least-squares. The weight function may be determined in block 510. For example, more weight may be given to points nearer to the point whose response is being estimated. Any weight function may be used in LOWESS for weighing the neighboring data points. For example, a tri-cube weight function may be used. The value of the regression function for that point is then obtained by evaluating the local polynomial using the explanatory variable (for the purpose of this disclosure, the single explanatory variable is the time variable) values for that data point.

The degree of local polynomial fitting may be determined in block 506. The local polynomial fitting to each subset of the data may be of low order, e.g., first degree (linear) or second degree (quadratic). A zero degree polynomial turns LOWESS into a weighted moving average which may work well for some situations, but may not always approximate the underlying function well. Polynomials with degree higher than quadratic, on the other hand, may yield models that are more suitable for global rather than local estimation and tend to over-fit as a local regression that is numerically unstable.

The local subsets of data used for each weighted least squares fit in LOESS may be determined at block 508 by a nearest-neighbor determination algorithm. The subset of data used in each weighted least-squares fit comprises a portion of points in the data set. A large portion produces the smoothest functions that wiggle the least in response to fluctuations in the data. A smaller portion provides a regression function that conforms more closely to the data. Those of ordinary skill in the art understand that data subsets that are too small may not be desirable since the regression function will eventually tend to model the random noise in the data. Thus, useful size of data subsets may be, for example, 0.25 to 0.5 of the total data set.

Figure 6:
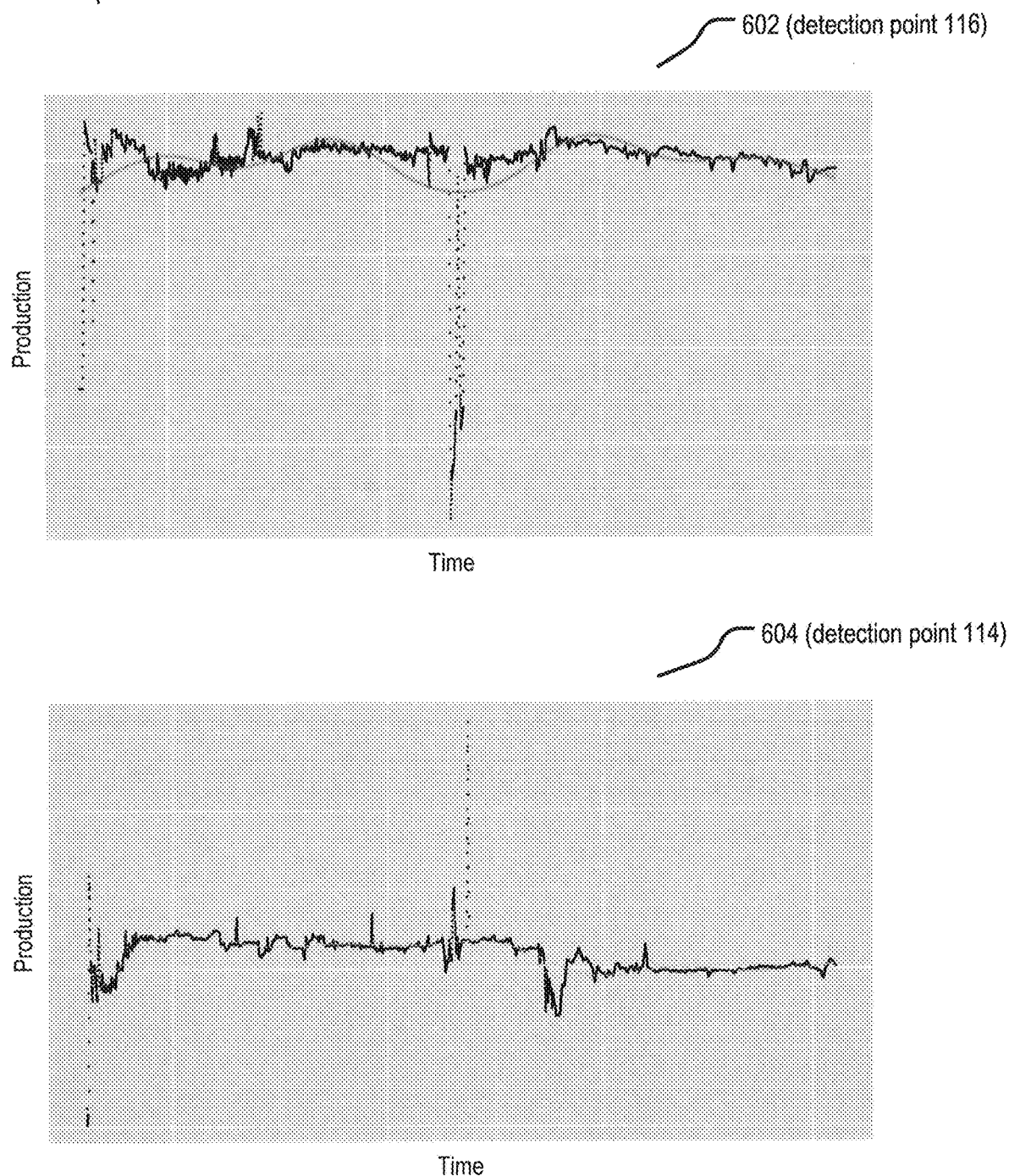
FIG. 6 shows interpolated historical production data.

FIG. 6 shows the interpolated results of the historical production data of FIG. 4, i.e., the modified production data of FIG. 3, on a predetermined time grid (one data point per hour) based on LOWESS. In particularly, 602 shows the interpolated historical production data corresponding to the historical production data analyzed at detection point 116 of FIG. 1, whereas 604 shows interpolated historical production data corresponding to the historical production data analyzed at detection point 114 of FIG. 1. The modified production data is a time series of production data having common timestamps (e.g., every hour during the operation of the plant) with the sampled historical sensor data for sensor parameters, i.e., 314 of FIG. 3.

Noise and abnormality reduction step in block 316 of FIG. 3 of the modified production data may be based on various noise filtering algorithms. For example, the noise and abnormality reduction of the modified production data may be based on Kalman filtering. Noises and abnormalities in the modified production data, particularly human errors in analysis and recording, may severely affect the quality and accuracy of the final model building based on regression algorithms. Some of the regression modeling techniques, such as Random Forest Regression can be very sensitive to statistical noise or data abnormality. Other regression model techniques, such as Generalized Linear Regression Modeling (GLRM) may be less sensitive to these noises and abnormalities in the data but the modeling accuracy may nevertheless be improved if noises and data abnormalities are filtered prior to modeling.

Kalman filtering, for example, may be used to pre-process the modified production data. In this case, the Kalman filter recursively uses a system's laws of motion from one state to another in time and multiple sequential modified production data (considered as measurements) to form an estimate of the system's state from one time to the next time. Estimates by Kalman filter, referred as estimated production data, is better than the any one measurement alone (data in the modified production data, also referred to as measured production data) because external factors that are not accounted for may introduce uncertainty into the measured (i.e., modified) production data. These external factors may be due to human analysis or recording errors in processing the historical production data and noises in sensors whose data were used for manual derivation of the historical production data (this is particularly true, for example, in a complex chemical reaction tower). Because, abnormalities in data typically do not occur repeatedly, they may be reduced to some extent by considering the prediction capability of production data from one time to the next based on the laws of motion of the system in addition to only the measured (modified) production data. The production data for one time predicted from the previous time based on the laws of motion is referred to as predicted production data. The estimated production data for a particular time may be based on weighted linear combination of the measured production data and the predicted production data for that time. Such estimated production data may contain reduced noises and abnormalities.

The modified production data as a function of time has a single state variable, i.e., the production (or production rate, or productivity, used interchangeably). The Kalman filtering problem here is thus a one-dimensional problem. The implementation below describes an exemplary use of Kalman filter to obtain better estimated production data at time tK based on measured production data at time tK and predicted production data for tK from estimated production data and its variance at time tK−1. In the particular example given in this disclosure, the time difference between tK and tK−1 is one hour. Here, . . . , K−1, K, K+1, . . . represent the numbering within the time series of interpolated production data (i.e., modified production data, considered as measured production data). The algorithm keeps track of the local variances at each time for estimated, measured, and predicted production data, as will become clear in the description below. The variances are represented by V with proper subscripts.

Figure 7:
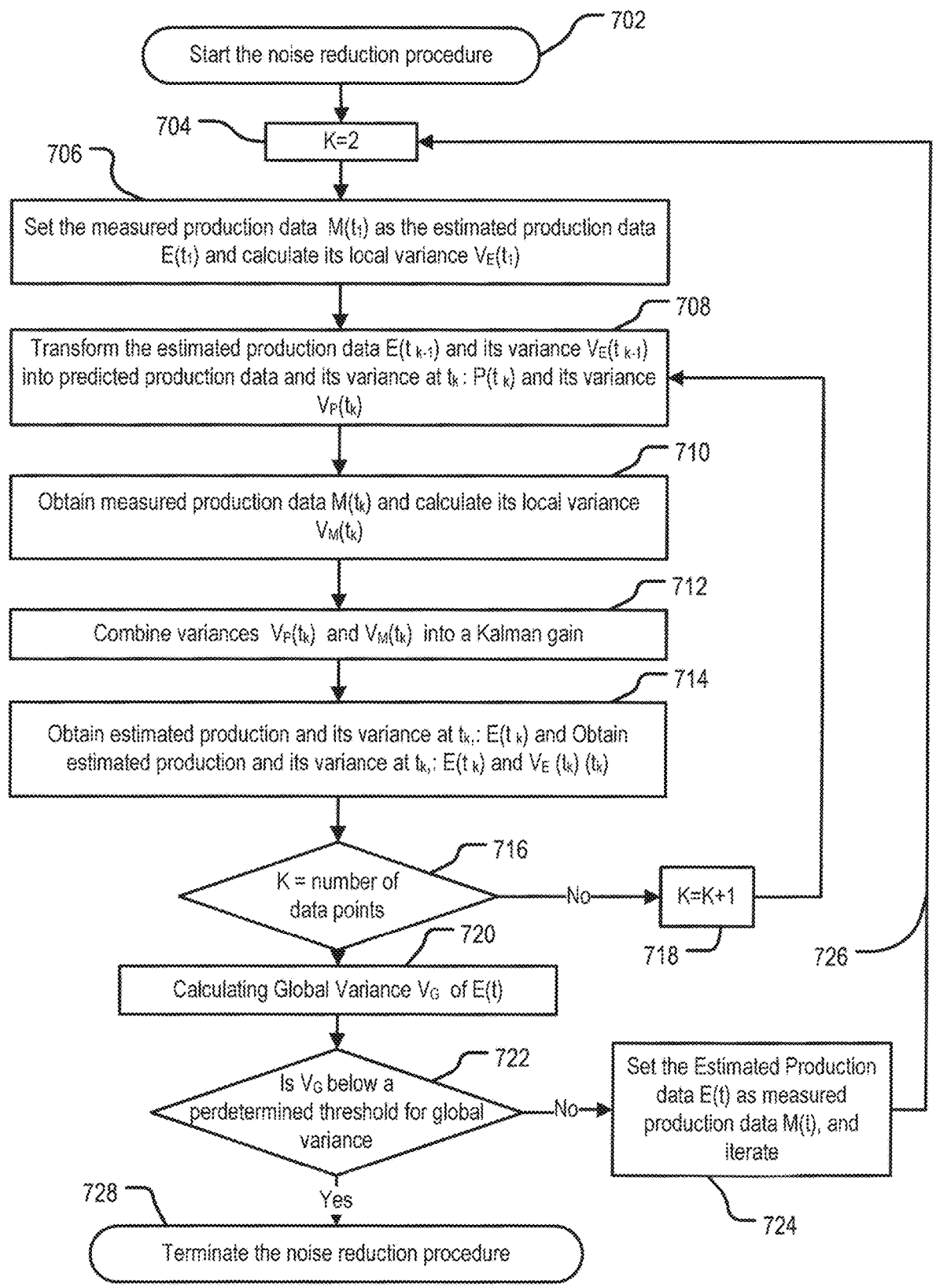
FIG. 7 is a flow chart for noise and abnormality reduction of the interpolated historical production data based on Kalman filtering.

FIG. 7 illustrates an exemplary flow diagram for Kalman filtering of the modified production data in a recursive process. In block 704, K is set at 2. That is, the Kalman filtering process began with estimating the second point in the time series of the modified production data (K=2) using the first data point in the modified production data (K=1) as the estimated production data for K=1. Thus, in block 706, the value of the estimated production data for t1, represented by E(t1), is given by the measured production data M(t1), and a local variance for estimated production data at t1, VE(t1), is given by a local variance of the measured production data VM(t1) calculated based on a preset number of neighboring (in time) measured production data. The local variance, for example, may be defined as a sum of square of differences among a predetermined number of local points.

In block 708, estimated production data E(t k−1) and its local variance VE(t k−1) is transformed into predicted production data and its variance for tk, namely, P(t k) and its local variance VP(tk) based on the laws of motion in time for the production data. As an example, the laws of motion in time for the production data may be determined by running a simple predefined smoothing of the measured production data (e.g., 20 points running average). In block 710, the measured production data M(tk) is obtained and its local variance VM(tk) is calculated using the predetermined number of neighboring measured production data. In block 712, predicted variance VP(tk) and measured variance VM(tk) are combined into a Kalman gain:

$$G(tk)=VP(tk)/(VP(tk)+VM(tk)).$$

The Kalman gain is thus between 0 and 1. When the measurement local variance is large at tk (e.g., there is data abnormality around tk), the Kalman gain approaches 0. But if the measurement are accurate (small noise and no abnormality) with small local variance, then the Kalman gain would approach 1. In block 714, the estimated production for tk, namely, E(t k), and its local variance VE (tk) are obtained as:

$$E(tk)=P(tk)+G(tk)(M(tk)-P(tk))$$

$$VE(tk)=VP(tk)(1-G(tk))$$

Thus, the predicted production data P(t k) (predicted from E(t k−1)) and measured production M(t k) are both considered in obtaining the estimated production data E(t k). The estimated production data E(t k) thus lies in between and is a weighted average of the predicted production data P(t k) and measured production M(t k). The noisier the measured data (and thus smaller Kalman gain), the more weight is placed on the predicted production data P(t k) and less weight is placed on the measured production data M(t k).

The estimated variance at tk, namely VE (tk), is reduced from the predicted variance VP (t k) by (1−G(tk)). Thus, the cleaner the measured data (larger G(tk) towards 1), the smaller the estimated variance VP (t k).

The process above runs through the entire measured production data set (for the first iteration, that would be the modified production data set) to obtain a new series of estimated production data, as illustrated by the loop formed by performing block 716, 718, and returning to block 708. This new series of estimated production data may then be viewed as measured data, as shown in block 724, and the above process may be performed iteratively for a second round, a third round, and so on. At the end of each round and in block 720, the global variance of the entire new series of estimated production data may be calculated. The global variance is compared to a predetermined global variance threshold in block 722. If the global variance is smaller than the predetermined global variance threshold, the iteration process stops at block 728. Otherwise, the next round of Kalman filtering is performed as shown by the looping arrow 726. The final time series of estimated production data E(t), may be set as the filtered production data 322 of FIG. 1 and used for the predictive model development based on machine learning algorithms in block 326 of FIG. 3.

Figure 8:
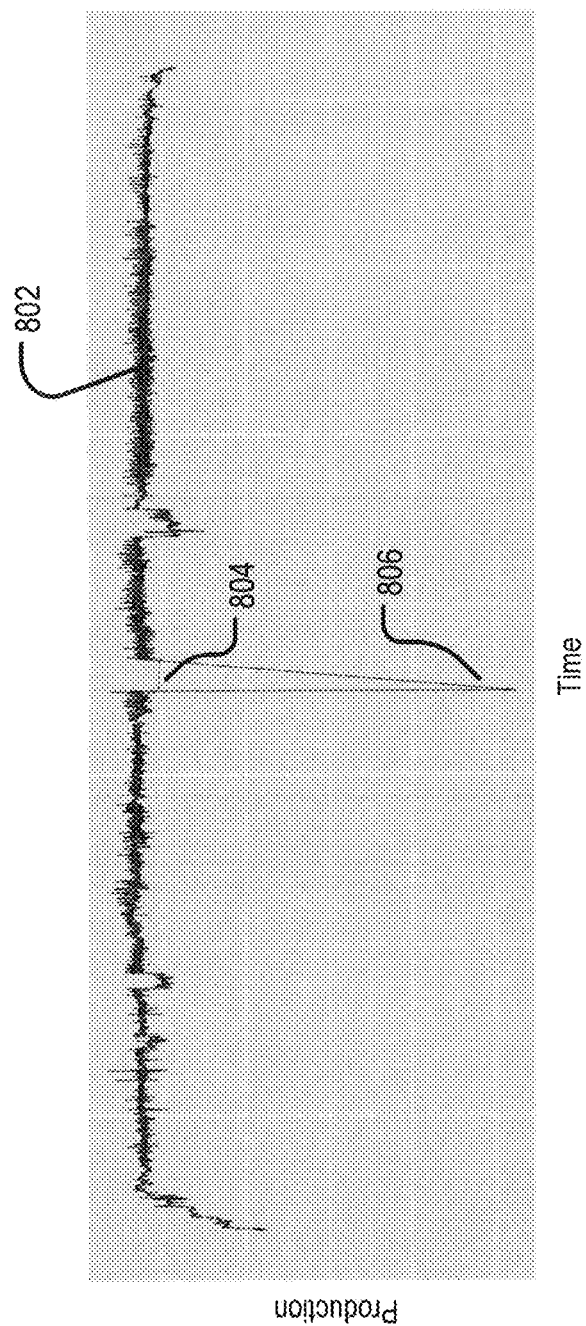
FIG. 8 shows a comparison between unfiltered and Kalman-filtered interpolated historical production data.

FIG. 8 show an example of modified production data 802 and corresponding filtered production data 804 using Kalman filtering described above. The filtered production data follows the major data trends in the modified production data. Noises and data abnormalities, e.g., as indicated by 806, are effective reduced.

Returning to FIG. 3, the sampled historical sensor data 314 may contain data for hundreds or thousands of parameters from various sensors distributed in the plant. Establishing a predictive model for production of the chemical product based on machine learning algorithms using all the parameters may be unnecessary and computationally infeasible. In addition, machine learning algorithm based on all these parameters will likely lead to over-fitting that models noise in the data rather than real features. Modeling the production of chemical product based on all sensor parameters is unnecessary also because not all the parameters are independent and various correlations may exist among the parameters, as described above.

Figure 9:
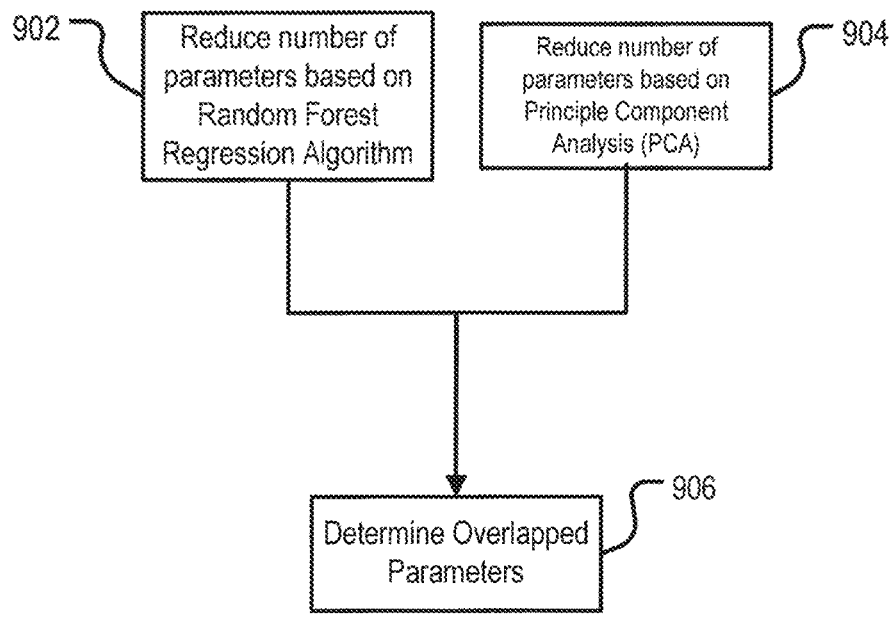
FIG. 9 is a flow chart of a method for dimensionality reduction of the sampled historical sensor data.

The correlation among the thousands of parameters may be exploited using dimensionality reduction techniques and the final set of reduced number of parameters may then be used for predictive model development. These techniques include but are not limited to Principle Component Analysis (PCA), Random Forest Algorithm (RFA), and Multi-Dimensional Scaling (MDS). The dimensionality reduction may be based on single or combination of these various approaches. For example, FIG. 9 illustrates steps for performing dimensionality reduction based on combination of RFA and PCA. Specifically, in block 902 and 904, the number of parameters is reduced using RFA and PCA, respectively and separately. The two resulting reduced parameters sets may be compared to obtain a common parameter set in block 906. The common parameter set, referred to herein as the subseries of sampled historical sensor data 324 of FIG. 3, in combination with the filtered production data 322 of FIG. 3, may be used as the corpus for predictive model development.

Figure 10:
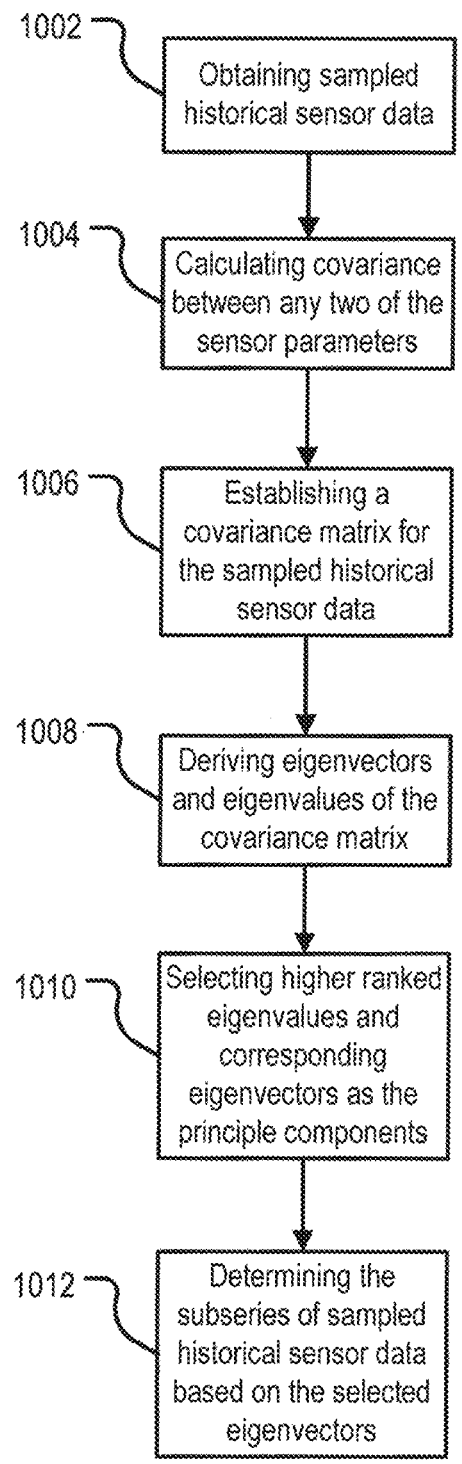
FIG. 10 is a flow chart of a method for principle component analysis.

PCA, for example, reduces the dimension of data to a smaller number of orthogonal linear combinations of the original parameters. FIG. 10 shows an exemplary flow chart for PCA. Specifically, in block 1002, sampled historical sensor data is obtained. In block 1004, covariance may be calculated between any two sensor parameters. Assume that there are x sensor parameters and there are N time slots in the sampled historical sensor data set (thus, series of sensor data for each sensor parameter contains N data). Covariance between the ith and jth sensor parameters $S_i$ and $S_j$, for example may be defined as:

$$V_{ij} = \frac{\sum_{k=1}^{N}(S_i(k)-\overline{S_i})(S_j(k)-\overline{S_j})}{N-1},$$

where $\overline{S_i}$ and $\overline{S_j}$ are the mean values for the ith and jth parameters, respectively. The matrix Vij thus represents the x by x covariance matrix for the sampled historical sensor parameters and is established in block 1006. In block 1008, eigenvalues and corresponding eigenvectors of the covariance matrix may be calculated. In block 1010, eigenvectors with higher eigenvalues may be selected as linear principle components (LPCs) and the rest of the eigenvectors may be discarded. For example, x eigenvalues and the corresponding LPCs may be retained. Each eigenvector is a linear combination of the x sensor parameters. These LPCs with higher eigenvalues can explain most of the variance. Through eigenvalue decomposition, the total variance of the sampled historical sensor data is equal to the sum of the eigenvalues of the variance matrix Vij. The number x of LPCs with higher eigenvalues to be retained may be determined by specifying a variance percentage threshold and requiring that the sum of the y retained eigenvalues is of higher proportion of the sum of all eigenvalues than the specified variance percentage threshold.

The LPCs are largely uncorrelated new variables constructed as linear combinations of original x sensor parameters and do not necessarily correspond to meaningful physical quantities. The reduced set of z physical sensor parameters may be further determined in block 1012. For example, in the selected eigenvectors of the covariance matrix Vij with higher eigenvalues, only components corresponding to a smaller number (than p) of physical sensor parameters are larger than some value predetermined by, for example, expert plant operators. Only those physical sensor parameters may be worth selecting. Further, among the physical sensors that correspond to large components in the selected eigenvectors, there may still be some remaining correlation. For example, two sensors may be in close proximity and thus the parameters they measure may go hand-in-hand. For another example, gas pressure and temperature may go hand-in-hand in a chamber. These correlations may either be recognized by examining the selected eigenvectors or be provided by the expert plant operator. Some of these physical sensor parameters may be redundant and thus can be further removed from the selected physical sensor parameters. As a result of block 1012, dimensionality reduction is achieved by retaining only the remaining z physical sensor parameters.

In another implementation, RFA may be used for dimensionality reduction for the sampled historical sensor data. Decision tree ensembles, also referred to as random forests, may be used for selection rather than classification. For example, shallow trees may be generated. Each tree may be trained on a small fraction of the sampled historical sensor data. If a sensor parameter is often selected as best split, it is likely an informative feature to retain. Based on the assemble of trees, a score for each sensor parameter is calculated by counting how many times the sensor parameter has been selected for a split and at which level of the trees it is selected for the split. The score quantifies the predictive ability of the sensor parameter. Sensor parameters with higher scores may be the most predictive and are thus retained. The rest of the parameters may be removed from the sampled historical sensor data to obtain the subseries of sampled historical sensor data.

Figure 11:
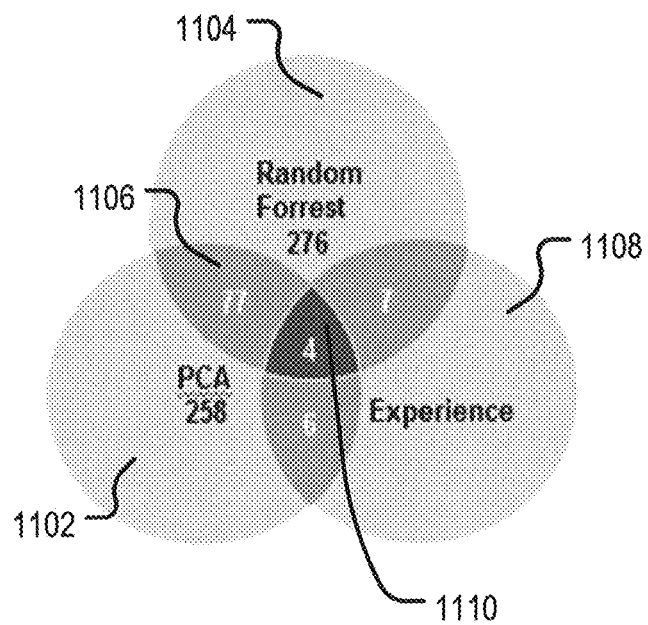
FIG. 11 illustrate sensor parameter selection for predictive modeling of styrene production in a styrene plant.

Either one of or both of the PCA and RFA dimensionality reduction may be performed and used to extract sensor parameters that correlate most with the filtered production data. For example, when both PCA and RFA are used, a common set of higher ranking parameter may be used for further predictive modeling. In one implementation, the ranking of the sensor parameters in PCA and RFA may be separately quantified and may be combined as a weighted average ranking. Sensor parameters may be selected based on the weighted average ranking from top to bottom. As shown by FIG. 11, in one exemplary PCA and RFA processing of a set of sampled historical sensor data and filtered production data, among 258 highest ranked sensor parameters determined by PCA (shown by 1102) and 276 highest ranked sensor parameters determined by RFA (shown by 1104), 77 parameters overlap, as shown by 1106. The 77 overlapping parameters may be ranked using weighted average and an even smaller number of highly ranked parameters, e.g., 33 parameters, may be selected for further predictive modeling.

In some further implementation, another set of parameters determined from experience of the engineers and operators in running the plant, shown by 1108 of FIG. 11, may be identified. In the particular example of FIG. 11, four of these parameters overlap with both the higher ranked PCA and RFA parameters. It may be preferable to include all these four parameters in the 33 parameters selected for predictive modeling.

The output of the processing steps of Kalman filtering and dimensionality reduction above is the filtered production data (322 of FIG. 3) and the dimensionality-reduced subseries of sampled historical sensor data (324 of FIG. 3). Production Index (PI) may then be model based on machine learning using various algorithms. For example, Generalized Linear Regression Modeling (GLRM) may be used. As an initial step of data processing, modeling based on machine learning algorithms using historical data typically segregate historical data into data sets for training, testing, and verification.

Figure 12:
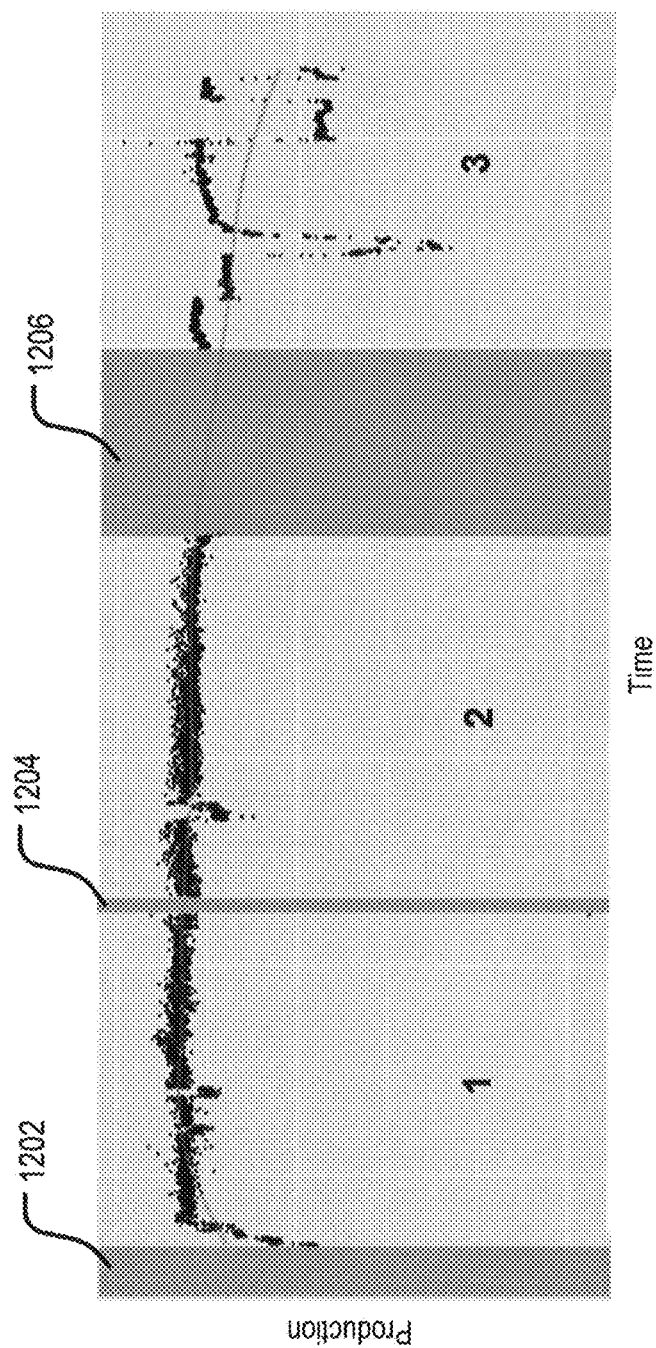
FIG. 12 illustrates data segmentation into training, testing, and verification data sets for predictive modeling based on machine learning algorithms.

FIG. 12 shows an example of data segregation for applying machine learning algorithms. Specifically, the filtered production data and the subseries of sampled historical sensor data may be divided into multiple time segments, such as segment 1, 2 and 3 of FIG. 12 (for simplicity, FIG. 12 only shows the filtered production data). Segment 1 for example, may be used as training corpus. Segment 2 may be used as testing data set during the regression model development. Once the model development is completed, data in segment 3 may be used to verify the quality and accuracy of the developed predictive model. Segment 3 of FIG. 12 is particularly suitable as data for verification of the PI model because, unlike segment 1 and 2, data in segment 3 exhibits large variation in the filtered styrene production data within the corresponding time period, indicating large variation of the operation condition for the plant, likely due to equipment tuning. If the predictive model developed based on relatively less varied data from segment 1 and segment 2 can accurately predict the production data for segment 3, it would indicate that the predictive model developed is of high quality. In this particular example, data segments 1, 2 and 3 are separated by equipment maintenance periods 1202, 1204, and 1206. The equipment maintenance period 1206, in particular, is prolonged and involves multiple equipment replacement and retooling. As such, segment 3 is especially suitable as a verification data set for the predictive model developed based on training data in segment 1 and test data in segment 2.

Those of ordinary skill in the art understand that although the implementation above segments the data into training set, test set and verification set after obtaining the subseries of sampled historical sensor data and filtered production data, data segmentation for model development may be made earlier such that the interpolation and noise filtering of historical production data, and the sampling and dimensionality reduction of the historical sensor data may be performed only on the training and test segments.

Figure 13:
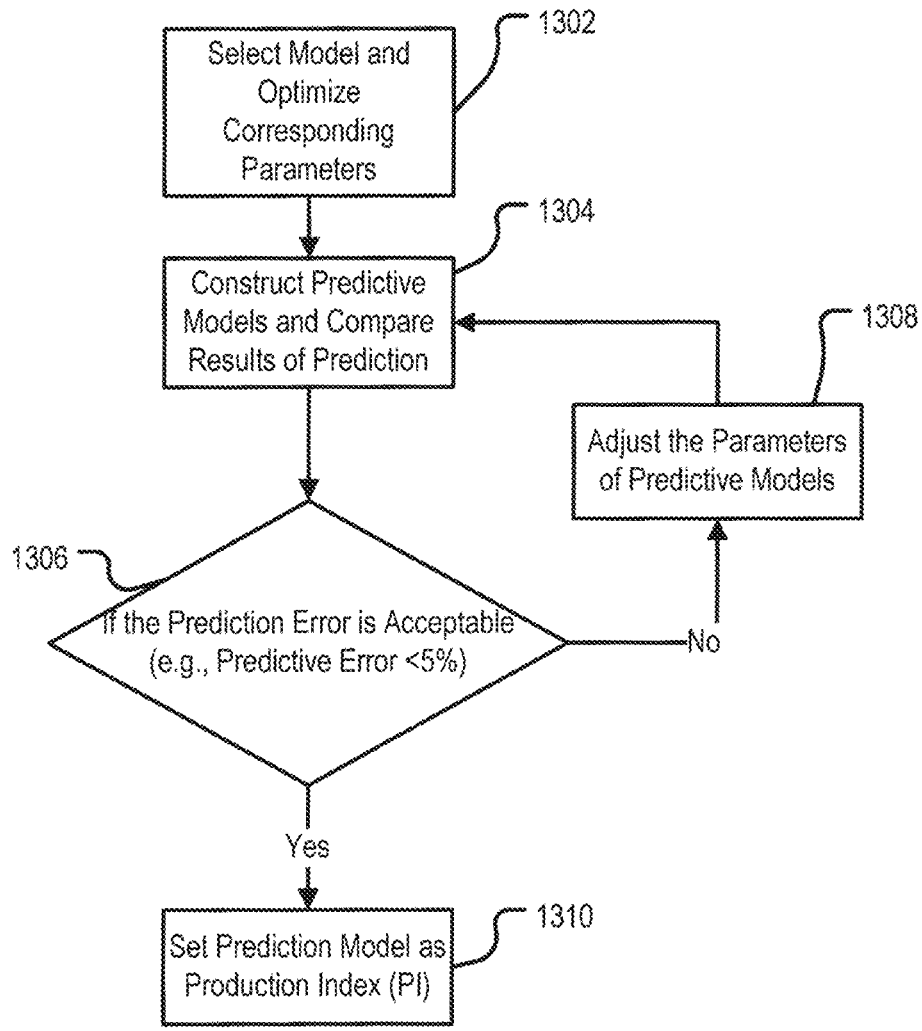
FIG. 13 is a flow chart for Product Index modeling based on machine learning algorithms.

Various machine learning algorithms may be used for the development of the production index (PI) for the chemical product. FIG. 13 illustrates the general predictive model development process. In block 1302, a machine learning regression algorithm is selected. For example, the machine learning algorithm may be based on Generalized Linear Regression Modeling (GLRM). It may alternatively be based on Random Forest Regression (RFR). Both regression algorithms are known in the art. Other regression algorithms are contemplated. In block 1304, predictive model is constructed based on the selected machine learning algorithm and used for making prediction on verification data set. In block 1306, it is determined whether the prediction conforms to actual verification data within a predetermined accuracy. If the predictive model is not accurate enough, the predictive model is adjusted in block 1308, and the model is refined in block 1304. If the predictive model is accurate enough, it is set as the PI in bock 1310 and the predictive modeling process ends.

Figure 14:
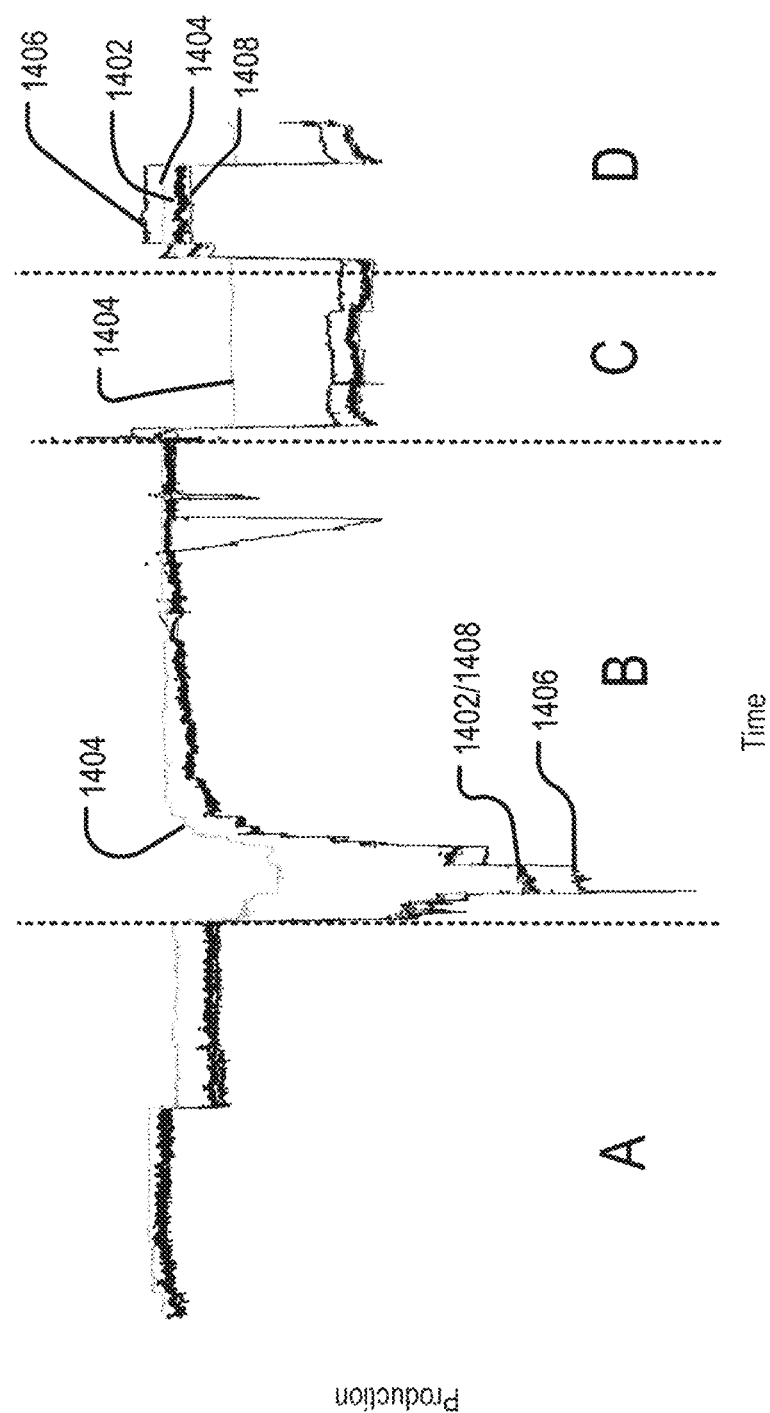
FIG. 14 illustrates the predictive accuracy of production index models developed based on various data processing and machine learning algorithms.

For verification of the PI, subseries of sampled historical sensor data for segment 3 of FIG. 12 is input into the PI and output is produced for predicted production data. FIG. 14 illustrates the prediction results using PIs developed based on various alternative data processing and options for machine learning algorithms described above. For example, curve 1408 is based on GLRM for machine learning and the Kalman filtering is used in reducing noise and abnormality in the historical production data used for training. Curve 1404 is based on RFR without Kalman filtering. Curve 1406 is based on GLRM without Kalman filtering. Compared with the measured production data in curve 1402, RFR without Kalman filtering provide the worst prediction, while GLRM with Kalman filtering provides excellent prediction. GLRM without Kalman filtering falls in the middle. The results is further illustrated in Table 1, which lists the average prediction error for regions A, B, C, and D of FIG. 14 for the three different prediction models above.

It can be seen that for relatively stable regions such as region A, GRM is excellent with or without Kalman filtering. For regions with large variation (due to equipment tuning, for example) such as region B, where data abnormality may degrade the accuracy of modeling, Kalman filtering greatly helps reducing the impact of data abnormality and producing a better predictive PI.

TABLE 1

| PIs | Time Period | | | | Average Error Rate |
|---|---|---|---|---|---|
| | A | B | C | D | |
| Kalman-GLRM | 1.34% | 2.46% | 1.98% | 2.33% | 2.03% |
| GLRM | 2.14% | 7.08% | 5.21% | 9.88% | 6.08% |
| RFR | 6.77% | 34.11% | 21.09% | 4.31% | 16.57% |

Figure 15:
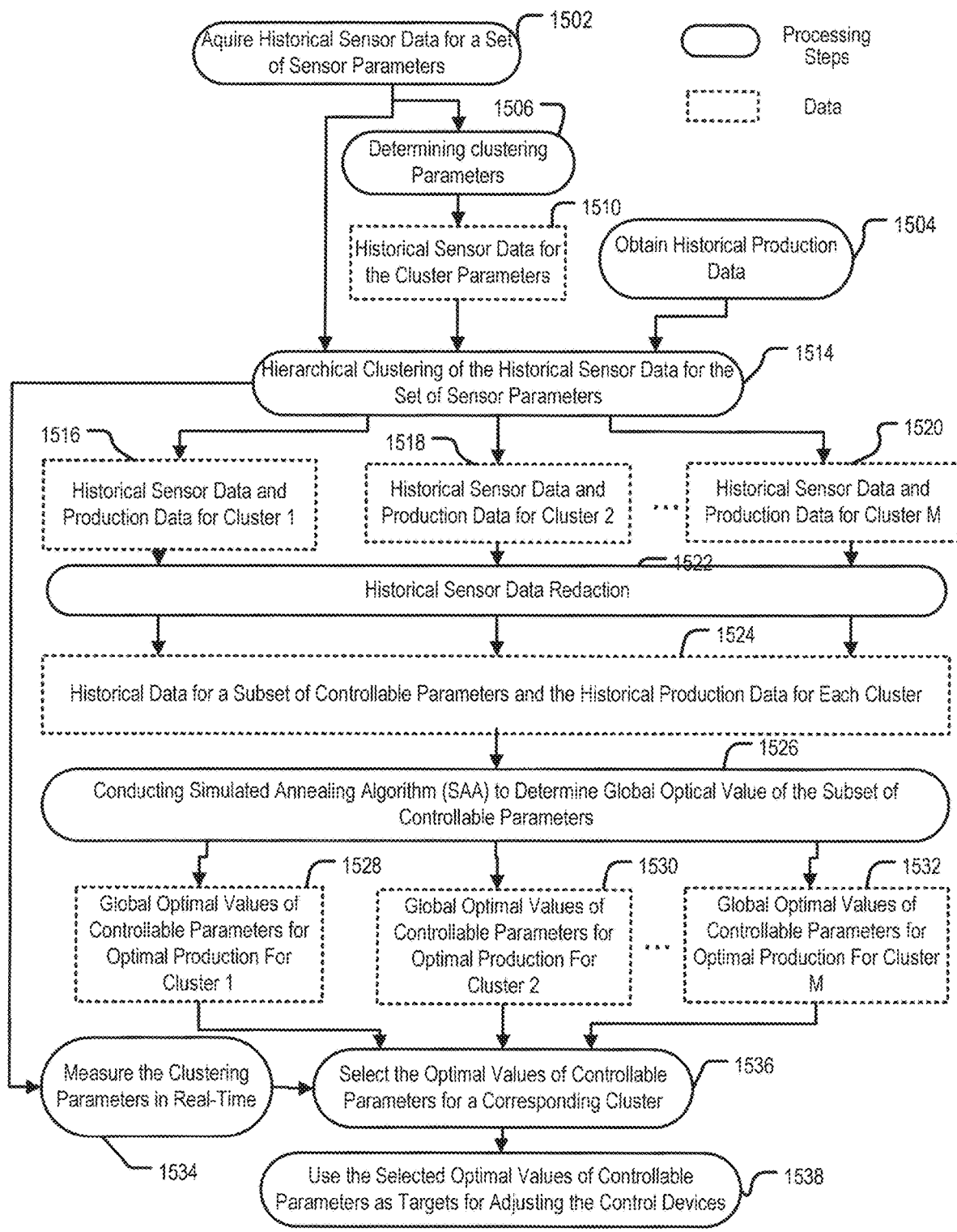
FIG. 15 is a process flow chart and data chart for optimizing controllable parameters for maximizing production of a chemical product in a chemical plant.

Turning now to production optimization, FIG. 15 shows a flow chart for determining optimal values of controllable sensor parameters for production of the chemical product. As described above, not all sensor parameters are directly controllable. Further, many of the sensor parameters are correlated to some extent. Thus, even if a sensor parameter is not directly controllable, it may be indirectly affected by the adjustment of a control device intended for directly controlling another sensor parameter. The correlation between the parameters may vary at different operation condition of the plant. The operation condition may be characterized by very few parameters that may be determined by experienced engineers and plant operators or through analysis of historical production and sensor data. Thus, optimal values of controllable parameters for maximize production of the chemical product may be obtained for each operation condition based on historical data clustered according to the values of the few operation condition-determining parameters (herein referred to as clustering parameters).

In block 1502 and 1504, historical sensor data for a set of sensor parameters and historical production data are respectively obtained from the historical record database. Clustering parameters are determined in block 1506. Data for the clustering parameters are then extracted from the historical sensor data in block 1510. In block 1514, the historical sensor data including the extracted data for the clustering parameters and the historical production data are hierarchically clustered, based on the values clustering parameters, into clusters of historical sensor and production data, clusters 1, 2, . . . , M, as shown by 1516, 1518, and 1520. In block 1522, only the historical sensor data for the controllable parameters are retained for each cluster. The cluster data 1516, 1518, and 1520 are thus redacted in block 1522 to a subset of controllable parameters and the historical production data 1524.

In block 1526, the redacted historical dataset for each cluster is processed using a suitable algorithm for determining the optimal values of the control parameters for maximal but stable production of the chemical product. As an exemplary algorithm, Simulated Annealing Algorithm (SAA) may be used for approximate global optimum and calculate the optimal values for the controllable parameters. SAA is used to find the highest stable plateau for the historical production data as a function of the controllable parameters. The highest stable plateau represents a global maximum. A stable plateau rather than a pointing peak of the historical production data as a function the controllable parameters (even if the pointing peak is higher than the plateau) is considered as a global maximum because, at a global maximum determined by a stable plateau, production of the chemical product is not overly sensitive to the controllable parameters and thus does not require overly precise control of these parameters, whereas these parameters need to be controlled precisely to keep the production at a peaky maximum. SAA may be based on any implementations known or unknown in the art.

The outputs of the clustering process are the global optimal values of the controllable parameters for each cluster, as shown by 1528, 1530, and 1532 of FIG. 15. These sets of values may be used as a basis for optimizing the operation of the chemical plant. For example, in block 1534, the clustering parameters may be measured in real-time and the measured values is designated with one of the clusters based on the clustering algorithm of block 1514. Once the cluster designation is determined, the corresponding optimal values for the controllable parameters may be selected in block 1536 from 1528, 1530, and 1532. The selected controllable parameter values may be used as targets for adjusting the control devices in the plant. The control of the control devices of the plant by the computing subsystem of 201 of FIG. 2 may be through the control communication interface 226 of FIG. 2. To maintain a control parameter to its target value, a feedback loop may be used for adjusting the corresponding control device.

Figure 16:
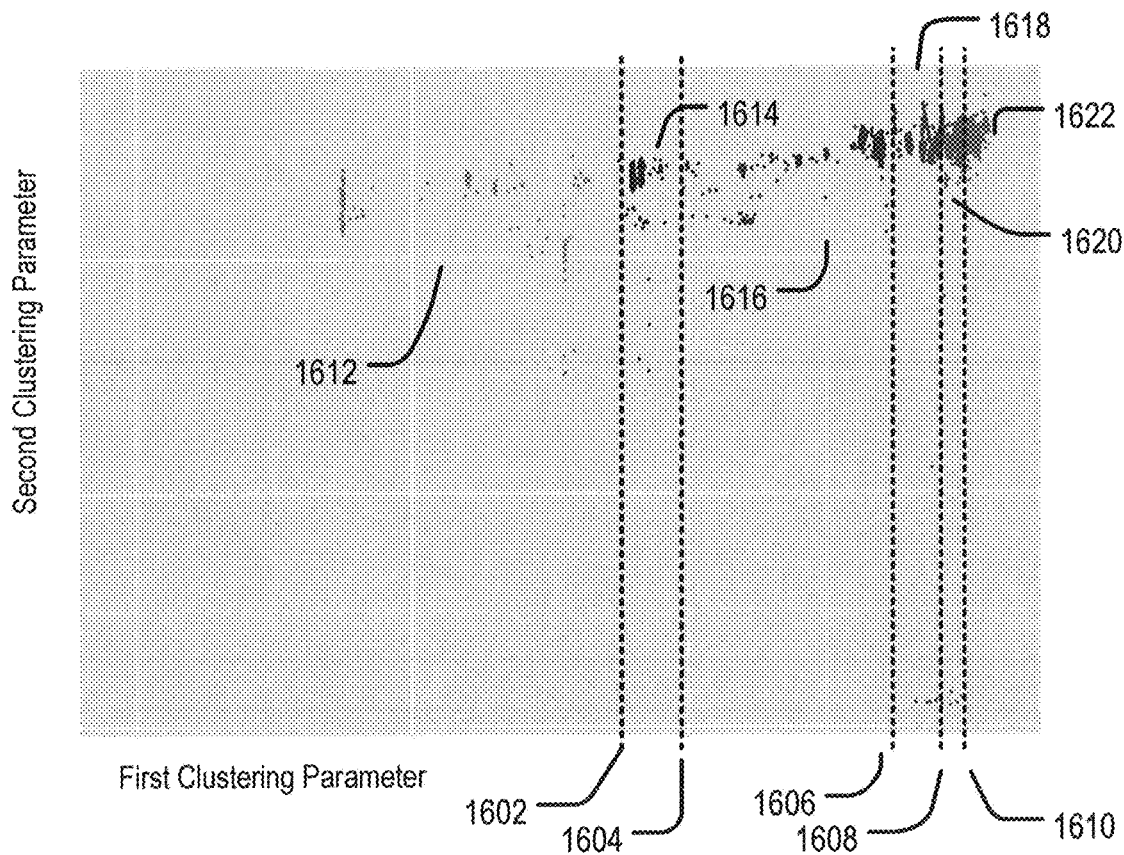
FIG. 16 illustrates clustering of historical production data.

For example, FIG. 16 shows historical clustering of historical production data for a styrene plant. Flow rate and temperature at entrance point, such as 112 of FIG. 1, are taken as the clustering parameters based on operation experience. The horizontal and vertical axes represent the first and second clustering parameter, respectively. Each point in FIG. 16 represents a combination of a value for the first clustering parameter and a value for the second clustering parameter. Once all combinations in the historical sensor data for these two parameters are identified (as one point for each combination) in FIG. 16, a clustering algorism may be used to divide the entire space of the two clustering parameters into sub regions. Each region represents one cluster. To avoid clustering based on spurious and abnormal data points, conditions may be set for the clustering algorithm. For example, a minimum number of data points for each cluster may be specified.

In the example of FIG. 16, the historical sensor data for the first and second parameters are mostly spread around the first clustering parameter. The resulting clusters may thus be separated by the vertical lines as shown as 1602, 1604, 1606, 1608, and 1610. Correspondingly, the values for the clustering parameters are clustered into clusters 1612, 1614, 1616, 1618, 1620, and 1622. Those of ordinary skill in the art understand that the clustering algorithm may be based on more than two clustering parameters. In addition, depending on the distribution of the combination of values of the clustering parameter, the division lines for the clusters may be more irregular than the simple vertical segmenting lines shown in FIG. 16.

Figure 17:
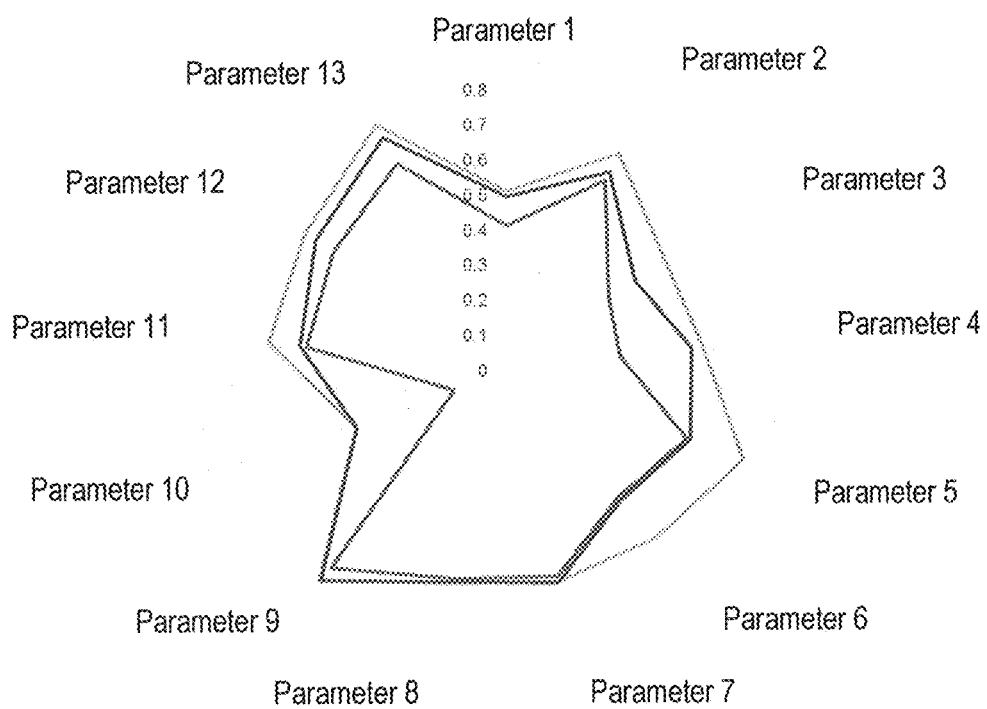
FIG. 17 shows an example of optimal control parameters determined using simulated annealing algorithm for one of the clusters of FIG. 16.

For the exemplary styrene plant with historical data segmented following FIG. 16, the redacted historical sensor data contains 13 controllable parameters. Table 2 shows the maximum value, minimum value, and optimal value determined by SAA of these 12 controllable parameters for cluster 1612 of FIG. 16. FIG. 17 shows a normalized result in a corresponding radar graph. Specifically, the outer line, middle, and inner lines show the maximum, optimal, and minimum values for the 13 controllable parameters for cluster 1612, respectively. Because SAA is aimed at identifying global stable maximum, the optimal values do not necessarily correspond to the absolute maximum, as clearly shown by Table 2 and FIG. 17.

TABLE 2

| Controllable parameters | Max. Value | Min Value | Optimal Value |
| --- | --- | --- | --- |
| Parameter 1 | 51050.30567 | 41442.25 | 49610 |
| Parameter 2 | 13918.21973 | 12207.81533 | 12750 |
| Parameter 3 | 109.74961 | 71.68504 | 89.16 |
| Parameter 4 | 56421.33906 | 32699.88 | 53050 |
| Parameter 5 | 14463.42 | 10985.80508 | 11242.2 |
| Parameter 6 | 128.2812 | 96.69752464 | 99.08 |
| Parameter 7 | 621.5180298 | 606.0794 | 623.7 |
| Parameter 8 | 625.2211639 | 612.1578 | 621.8 |
| Parameter 9 | 801.2750702 | 751.7804 | 795.6 |
| Parameter 10 | 45.59494495 | 15.93115 | 45.43 |
| Parameter 11 | 1.356515938 | 1.143650591 | 1.1794 |
| Parameter 12 | 13.85422173 | 11.92081356 | 13.11 |

The methods, devices, processing, frameworks, circuitry, and logic described above may be implemented in many different ways and in many different combinations of hardware and software. For example, all or parts of the implementations may the circuitry 224 of FIG. 2 that includes instruction processor 232 of FIG. 1, such as a Central Processing Unit (CPU), microcontroller, or a microprocessor; or as an Application Specific Integrated Circuit (ASIC), Programmable Logic Device (PLD), or Field Programmable Gate Array (FPGA); or as circuitry that includes discrete logic or other circuit components, including analog circuit components, digital circuit components or both; or any combination thereof. The circuitry may include discrete interconnected hardware components or may be combined on a single integrated circuit die, distributed among multiple integrated circuit dies, or implemented in a Multiple Chip Module (MCM) of multiple integrated circuit dies in a common package, as examples.

Accordingly, the circuitry may store or access instructions for execution, or may implement its functionality in hardware alone. The instructions may be stored in a tangible storage medium that is other than a transitory signal, such as a flash memory, a Random Access Memory (RAM), a Read Only Memory (ROM), an Erasable Programmable Read Only Memory (EPROM); or on a magnetic or optical disc, such as a Compact Disc Read Only Memory (CDROM), Hard Disk Drive (HDD), or other magnetic or optical disk; or in or on another machine-readable medium. A product, such as a computer program product, may include a storage medium and instructions stored in or on the medium, and the instructions when executed by the circuitry in a device may cause the device to implement any of the processing described above or illustrated in the drawings.

The implementations may be distributed. For instance, the circuitry may include multiple distinct system components, such as multiple processors and memories, and may span multiple distributed processing systems. Parameters, databases, and other data structures may be separately stored and controlled, may be incorporated into a single memory or database, may be logically and physically organized in many different ways, and may be implemented in many different ways. Example implementations include linked lists, program variables, hash tables, arrays, records (e.g., database records), objects, and implicit storage mechanisms. Instructions may form parts (e.g., subroutines or other code sections) of a single program, may form multiple separate programs, may be distributed across multiple memories and processors, and may be implemented in many different ways. Example implementations include stand-alone programs, and as part of a library, such as a shared library like a Dynamic Link Library (DLL). The library, for example, may contain shared data and one or more shared programs that include instructions that perform any of the processing described above or illustrated in the drawings, when executed by the circuitry.

Returning to FIG. 2, the communication interfaces, such as the data communication interface 230 and control communication interface 226 of FIG. 2 may be an interface for direct communicating or communication via a computer networks, which may be same or different from the communication network 222. All communication networks herein may be based on any type of connection such as a Wi-Fi connection, Bluetooth connection, Near Frequency Communication connection, telecommunications connection, internet connection, wired Ethernet connection, or the like, alone or in combination. Specifically, the communication interfaces 226 and 230 may include wireless transmitters and receivers ("transceivers") and any antennas used by the transmit/receive circuitry of the transceivers. The transceivers and antennas may support Wi-Fi network communications, for instance, under any version of IEEE 802.11, e.g., 802.11n or 802.11ac. The communication interfaces 226 and 230 may also include wireline transceivers. The wireline transceivers may provide physical layer interfaces for any of a wide range of communication protocols, such as any type of Ethernet, data over cable service interface specification (DOCSIS), digital subscriber line (DSL), Synchronous Optical Network (SONET), or other protocol.

The computing subsystem 201 of FIG. 2 may also optionally include a disk drive unit for accepting a computer readable medium. The computing sub readable medium may include a set of instructions that are executable by the CPU 232, and/or the computer readable medium may be utilized by the computing subsystem 201 as additional memory storage.

In a particular embodiment, the disk drive unit may include a computer-readable medium in which one or more sets of instructions, such as software, can be embedded. Further, the instructions may embody one or more of the methods, processes, or logic as described herein. In a particular embodiment, the instructions may reside completely, or partially, within the memory 234 during execution by the computing subsystem 201.

In accordance with various embodiments of the present disclosure, the methods described herein may be implemented by software programs executable by a computer system. Further, in an exemplary, non-limited embodiment, implementations can include distributed processing, component/object distributed processing, and parallel processing. Alternatively, virtual computer system processing can be constructed to implement one or more of the methods or functionality as described herein.

The term "computer-readable medium" includes a single medium or multiple media, such as a centralized or distributed database, and/or associated caches and servers that store one or more sets of instructions. The term "computer-readable medium" shall also include any tangible medium that is capable of storing, encoding or carrying a set of instructions for execution by a processor or that cause a computer system to perform any one or more of the methods or operations disclosed herein.

In a particular non-limiting, exemplary embodiment, the computer-readable medium can include a solid-state memory such as a memory card or other package that houses one or more non-volatile read-only memories, such as flash memory. Further, the computer-readable medium can be a random access memory or other volatile re-writable memory. Additionally, the computer-readable medium can include a magneto-optical or optical medium, such as a disk or tapes or other storage device to capture information communicated over a transmission medium. The computer readable medium may be either transitory or non-transitory.

The principles described herein may be embodied in many different forms. Not all of the depicted components may be required, however, and some implementations may include additional components. Variations in the arrangement and type of the components may be made without departing from the spirit or scope of the claims as set forth herein. Additional, different or fewer components may be provided.

Reference throughout this specification to "one example," "an example," "examples," "one embodiment," "an embodiment," "example embodiment," or the like in the singular or plural means that one or more particular features, structures, or characteristics described in connection with an embodiment or an example is included in at least one embodiment or one example of the present disclosure. Thus, the appearances of the phrases "in one embodiment," "in an embodiment," "in an example embodiment," "in one example," "in an example," or the like in the singular or plural in various places throughout this specification are not necessarily all referring to the same embodiment or a single embodiment. Furthermore, the particular features, structures, or characteristics may be combined in any suitable manner in one or more embodiments or examples.

The terminology used in the description herein is for the purpose of describing particular examples only and is not intended to be limiting. As used herein, the singular forms "a," "an," and "the" are intended to include the plural forms as well, unless the context clearly indicates otherwise. Also, as used in the description herein and throughout the claims that follow, the meaning of "in" includes "in" and "on" unless the context clearly dictates otherwise. It will also be understood that the term "and/or" as used herein refers to and encompasses any and all possible combinations of one or more of the associated listed items. It will be further understood that the terms "may include," "including," "comprises," and/or "comprising," when used in this specification, specify the presence of stated features, operations, elements, and/or components, but do not preclude the presence or addition of one or more other features, operations, elements, components, and/or groups thereof.

It should be noticed that, the steps illustrated in the flowchart of the drawings may be performed in a set of computer devices using executable program code. And the order of the steps may be different from that in the drawings under some status, although an example logic order is shown in the flowchart.

The purpose, technical proposal and advantages in the examples of the present disclosure will be clear and complete from the following detailed description when taken in conjunction with the appended drawings. The examples described thereinafter are merely a part of examples of the present disclosure, not all examples. Persons skilled in the art can obtain all other examples without creative works, based on these examples.

The numbers disclosed in tables in this disclosure are merely for illustrative purpose. The numbers may have units of measure that may be omitted from this disclosure. The illustrative numbers in tables may be used to illustrate the selection of the controllable parameters for equipment operation safety. The unit of measure for each number may or may not be relevant for selecting controllable parameters.

It is to be understood that, all examples provided above are merely some of the preferred examples of the present disclosure. For one skilled in the art, the present disclosure is intended to cover various modifications and equivalent arrangements included within the principle of the disclosure.

What is claimed is:

1. A system for predicting real-time production of a chemical product in a plant based on a subset among a set of parameters each monitored by one of a corresponding set of sensors at one of a corresponding set of measurement frequencies, the system comprising:
   a memory;
   a communication interface;
   circuitry in communication with the memory and the communication interface, the circuitry configured to:
      acquire, via the communication interface, multiple series of timestamped historical sensor data, each series corresponding to one of the set of parameters taken by a corresponding sensor among the set of sensors at a corresponding measurement frequency of the set of measurement frequencies during a time period;
      obtain a series of timestamped and indirectly measured historical production data for the chemical product during the time period having an indirect measurement frequency smaller than the set of measurement frequencies corresponding to the set of parameters;
      sample the multiple series of timestamped historical sensor data of the set of parameters to obtain multiple corresponding sampled series of historical sensor data of the set of parameters having a common series of sampled timestamps;

interpolate the series of historical production data based on a local smoothing algorithm to obtain a series of modified production data having a series of timestamps corresponding to the common series of sampled timestamps;

filter the series of modified production data to reduce noise or abnormality in the series of modified production data and obtain a series of filtered production data;

separately apply a first dimensionality reduction algorithm and a second dimensionality reduction algorithm on the multiple series of sampled historical sensor data using the series of filtered production data to respectively select a first subset and a second subset of parameters among the set of parameters, and select the subset of parameters from an overlap between the first subset and second subset of the set of parameters and corresponding selected series of sampled historical sensor data;

develop a predictive model for production of the chemical product as a function of the selected subset of parameters and the corresponding selected series of sampled historical sensor data;

store the predictive model in the memory;

obtain real-time readings during production of the chemical product from a subset of sensors corresponding to the subset of parameters; and predict production of the chemical product based on the predictive model and the real-time readings of the subset of parameters from the subset of sensors.

2. The system of claim 1, wherein the local smoothing algorithm is based on locally weighted scatterplot smoothing.

3. The system of claim 1, wherein to filter the series of modified production data to reduce noise or abnormality is based on Kalman filtering.

4. The system of claim 3, wherein the Kalman filtering is of a single dimension.

5. The system of claim 1, wherein one of the first dimensionality reduction algorithm and the second dimensionality reduction algorithm comprises a random forest algorithm (RFA).

6. The system of claim 5, wherein the other dimensionality reduction algorithm comprises a principle component analysis (PCA).

7. The system of claim 1, wherein the one of the first dimensionality reduction algorithm and the second dimensionality reduction algorithm comprises a PCA.

8. The system of claim 1, wherein developing the predictive model of production of the chemical product is based on generalized linear regression.

9. A method for predicting real-time production of a chemical product in a plant based on a subset among a set of parameters each monitored by one of a corresponding set of sensors at one of a corresponding set of measurement frequencies, the method comprising:

acquiring multiple series of timestamped historical sensor data, each series corresponding to one of the set of parameters taken by a corresponding sensor of the set of sensors at a corresponding measurement frequency of the set of measurement frequencies during a time period;

obtaining a series of timestamped and indirectly measured historical production data for the chemical product during the time period having an indirect measurement frequency smaller than the set of measurement frequencies corresponding to the set of parameters;

sampling the multiple series of timestamped historical sensor data of the set of parameters to obtain multiple corresponding sampled series of historical sensor data of the set of parameters having a common series of sampled timestamps;

interpolating the series of historical production data based on a local smoothing algorithm to obtain a series of modified production data having a series of timestamps corresponding to the common series of sampled timestamps;

filtering the series of modified production data to reduce noise or abnormality in the series of modified production data and obtain a series of filtered production data;

separately applying a first dimensionality reduction algorithm and a second dimensionality reduction algorithm on the multiple series of sampled historical sensor data using the series of filtered production data to respectively select a first subset and a second subset of parameters among the set of parameters, and select the subset of parameters from an overlap between the first subset and second subset of the set of parameters and corresponding selected series of sampled historical sensor data;

developing a predictive model of production of the chemical product as a function of the selected subset of parameters and the corresponding selected series of sampled historical sensor data;

obtaining real-time readings during production of the chemical product from a subset of sensors corresponding to the subset of parameters; and predicting production of the chemical product based on the predictive model and the real-time readings of the subset of parameters from the subset of sensors.

10. The method of claim 9, wherein the local smoothing algorithm is based on locally weighted scatterplot smoothing.

11. The method of claim 9, wherein filtering the series of modified production data to reduce noise or abnormality is based on Kalman filtering.

12. The method of claim 11, wherein the Kalman filtering is of a single dimension.

13. The method of claim 9, wherein the one of the first dimensionality reduction algorithm and the second dimensionality reduction algorithm comprises a random forest algorithm (RFA).

14. The method of claim 13, wherein the other dimensionality reduction algorithm comprises a principle component analysis (PCA).

15. The method of claim 9, wherein the one of the first dimensionality reduction algorithm and the second dimensionality reduction algorithm comprises a PCA.

16. The method of claim 9, wherein developing the predictive model of production of the chemical product is based on generalized linear regression.

17. A method for controlling production of a chemical product in a plant by controlling a subset of controllable parameters among a set of parameters each monitored by one of a corresponding set of sensors, the method comprising:

acquiring multiple time series of historical sensor data, each series corresponding to one of the set of parameters taken by a corresponding sensor of the set of sensors;

obtaining a time series of historical production data for the chemical product corresponding to the multiple time series of historical sensor data for the set of parameters;

determining at least two empirical operation-critical parameters among the set of parameters taken by the corresponding set of sensors as clustering parameters;

clustering hierarchically the multiple series of historical sensor data and the corresponding production data according to the at 1st two clustering parameters to obtain a set of data clusters, each data cluster corresponding to a range of values for the clustering parameters and comprising multiple sub-time series of historical sensor data for the set of parameters and corresponding sub time-series of historical production data for the chemical product;

for each data cluster of the set of data clusters:
extracting from the multiple sub-time series of historical sensor data for the set of parameters in the data cluster a redacted set of multiple sub-time series of historical sensor data for the subset of controllable parameters; and determining, for the data cluster, global optimal values for each of the subset of controllable parameters for optimizing production of the chemical product by performing a simulated annealing algorithm having an input comprising the set of multiple sub-time series of historical sensor data for the subset of controllable parameters and the sub-time series of historical production data for the chemical product;

monitoring real-time values of the clustering parameters;

determining a real-time operating condition for the plant corresponding a cluster determined by the real-time values of the clustering parameters; and controlling a set of adjustable control devices to adjust the subset of controllable parameters according to the global optimal values of the subset of controllable parameters for the real-time operating condition.

18. The method of claim 17, wherein each data cluster of the set of data clusters comprises at least a predetermined number of time series.

* * * * *